United States Patent
Bonmassar et al.

(10) Patent No.: US 10,327,701 B2
(45) Date of Patent: Jun. 25, 2019

(54) APPARATUSES AND METHODS FOR ELECTROPHYSIOLOGICAL SIGNAL DELIVERY AND RECORDING DURING MRI

(75) Inventors: Giorgio Bonmassar, Lexington, MA (US); Patrick L. Purdon, Cambridge, MA (US)

(73) Assignee: The General Hospital Corporation, Boston, MA (US)

(*) Notice: Subject to any disclaimer, the term of this patent is extended or adjusted under 35 U.S.C. 154(b) by 1404 days.

(21) Appl. No.: 11/913,641

(22) PCT Filed: Nov. 21, 2005

(86) PCT No.: PCT/US2005/042401
§ 371 (c)(1),
(2), (4) Date: Jun. 12, 2008

(87) PCT Pub. No.: WO2006/121469
PCT Pub. Date: Nov. 16, 2006

(65) Prior Publication Data
US 2008/0306397 A1    Dec. 11, 2008

Related U.S. Application Data

(60) Provisional application No. 60/678,629, filed on May 6, 2005.

(51) Int. Cl.
*A61B 5/0478* (2006.01)
*A61B 5/00* (2006.01)
*A61B 5/11* (2006.01)

(52) U.S. Cl.
CPC ........ *A61B 5/6814* (2013.01); *A61B 5/0478* (2013.01); *A61B 5/721* (2013.01); *A61B 5/1102* (2013.01)

(58) Field of Classification Search
CPC ................ A61B 5/0476; A61B 5/0482
(Continued)

(56) References Cited

U.S. PATENT DOCUMENTS

| 4,195,643 A | * | 4/1980 | Pratt, Jr. | 600/592 |
| 4,448,199 A | * | 5/1984 | Schmid | 600/393 |

(Continued)

FOREIGN PATENT DOCUMENTS

| WO | WO 2004/036379 A2 | 4/2004 |
| WO | WO 2004/047632 A1 | 6/2004 |

OTHER PUBLICATIONS

"Recording of EEG during fMRI experiments: patient safety" by L. Lemieux et al., Magnetic Resonance in Medicine, 38 (6): 943-952, 1997.*

(Continued)

*Primary Examiner* — Etsub D Berhanu
(74) *Attorney, Agent, or Firm* — Quarles & Brady LLP

(57) ABSTRACT

Methods, systems and arrangements are provided for obtaining electroencephalograph ("EEG") EEG signals from a patient e.g., during a concurrent EEG/MRI examination of the patient. The methods, systems and arrangements include a cap made of conductive inks with sensor positions for attaching a plurality of sensors to the patient's head. The sensors can include electrodes as well as motion sensors for improving EEG signal quality and MRI image quality in the presence of motion noise and other artifacts within the MRI environment. The electrodes may be composed of conductive inks, and can be used in high magnetic fields due to a weak interaction with the RF fields generated by the MRI scanner. The exemplary methods, systems and arrangements can achieve lower SAR and lower temperature increase, as compared to conventional electrodes.

23 Claims, 24 Drawing Sheets

(58) Field of Classification Search
USPC ........ 600/372–373, 386, 388, 393, 395–396, 600/410–411, 527, 382, 544–545; 439/909
See application file for complete search history.

(56) References Cited

U.S. PATENT DOCUMENTS

| | | | | |
|---|---|---|---|---|
| 5,215,088 | A | * | 6/1993 | Normann ............ A61B 5/04001 600/377 |
| 5,851,438 | A | * | 12/1998 | Chan .................... A61N 1/0436 252/511 |
| 6,032,063 | A | * | 2/2000 | Hoar et al. .................... 600/372 |
| 6,032,065 | A | * | 2/2000 | Brown .......................... 600/383 |
| 6,708,051 | B1 | * | 3/2004 | Durousseau .................. 600/383 |
| 6,740,214 | B1 | * | 5/2004 | Dobson et al. ............. 204/403.1 |
| 7,286,871 | B2 | | 10/2007 | Cohen |
| 2002/0128798 | A1 | | 9/2002 | Lange et al. |
| 2002/0156357 | A1 | | 10/2002 | Axelgaard |
| 2003/0088167 | A1 | | 5/2003 | Fendrock et al. |
| 2003/0130585 | A1 | * | 7/2003 | Wenger .............. A61B 5/04085 600/509 |
| 2005/0054941 | A1 | * | 3/2005 | Ting .................... A61B 5/0408 600/529 |

OTHER PUBLICATIONS

"Resistive Tapered Stripline (RTS) in Electroencephalogram Recordings During MRI" by Bonmassar, IEEE Transactions on Microwave Theory and Techniques, vol. 52, No. 8, Aug. 2004.*
"Acquiring simultaneous EEG and functional MRI" by Goldman et al., Clinical Neurophysiology, vol. 111, pp. 1974-1980, 2000.*
"Multimodal Neuroimaging with Simultaneous Electroencephalogram and High-Field Functional Magnetic Resonance Imaging" by Patrick L. Purdon, Doctoral Dissertation, 2005.*
Angelone et al. On the effect of resistive EEG electrodes and leads during 7 T MRI: simulation and temperature measurement studies. Magnetic Resonance Imaging 24 (2006) 801-812.*
International Search Report and Written Opinion dated Jun. 14, 2006 in connection with International Patent Application No. PCT/US2005/042401.

* cited by examiner

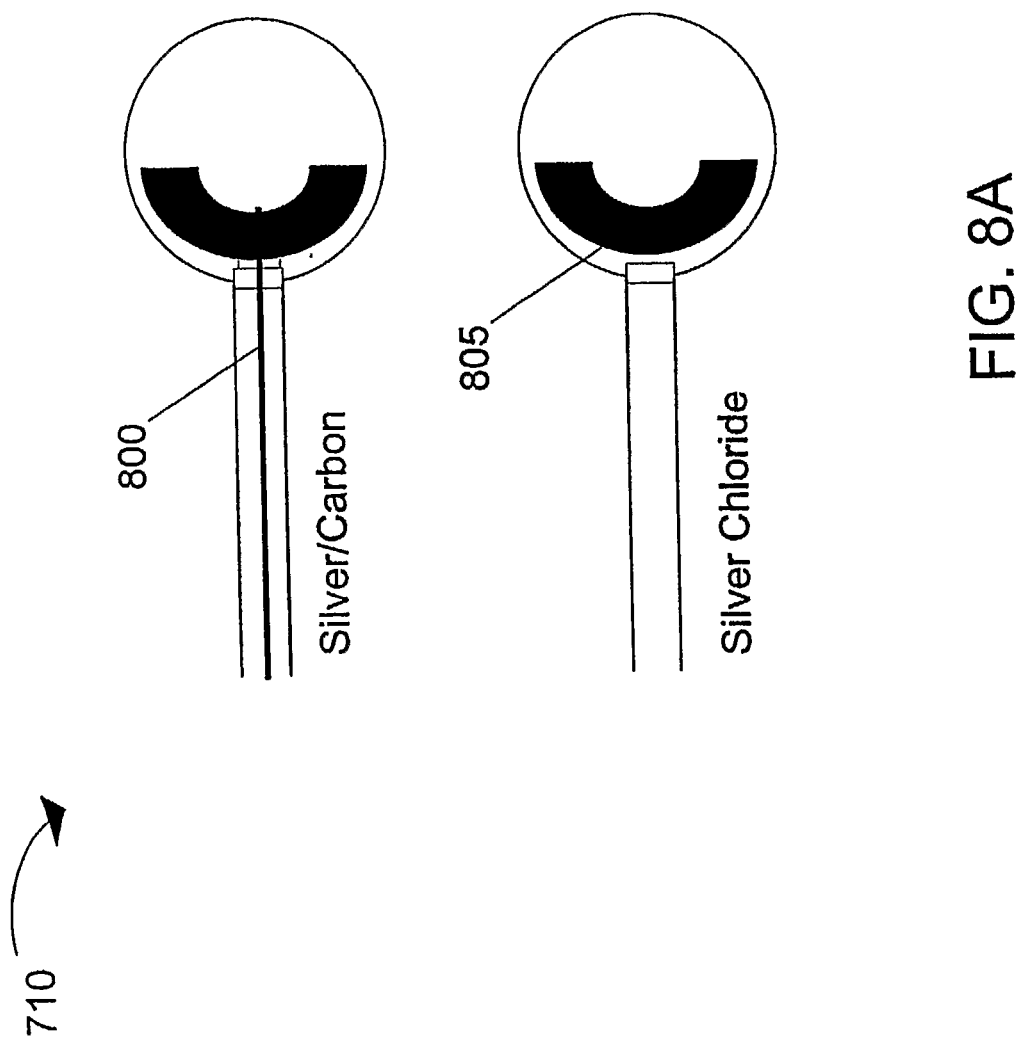

APPARATUSES AND METHODS FOR ELECTROPHYSIOLOGICAL SIGNAL DELIVERY AND RECORDING DURING MRI

CROSS-REFERENCE TO RELATED APPLICATIONS

The present application claims priority from 60/678,629 filed May 6, 2005. This application also relates to International Publication No. WO 03/073929, entitled "Electroencephalograph Sensor for Use with Magnetic Resonance Imaging and Methods Using Such Arrangements," and published on Sep. 12, 2003, and International Publication No. WO 2004/047632, entitled "Apparatus and Method for Ascertaining and Recording Electroplysiological Signals," published on Jun. 10, 2004, both of which are hereby incorporated by reference in their entireties.

STATEMENT REGARDING FEDERALLY SPONSORED RESEARCH

This invention was made with United States Government support under Grant No. EB000522 and Grant No. EB002459 awarded by the National Institutes of Health. The United States Government has certain rights in this invention.

FIELD OF THE INVENTION

The present invention relates generally to the delivery and recording of electrophysiological signals during Magnetic Resonance Imaging ("MRI"). More specifically, the present invention provides apparatuses and methods for the delivery and recording of electrophysiological brain signals during MRI using a variable impedance electrode arrangement with fixed relative lead layout and motion sensors provided in a conductive ink head cap.

BACKGROUND OF THE INVENTION

Advances in brain imaging technologies have made it possible for medical personnel to observe, extract, record, and graphically display electrophysiological signals that reflect brain activity in specific brain regions. These signals may be analyzed to detect many brain-related conditions, including spinal cord injuries, stroke, epilepsy, sleep disorders, brain death, and a variety of brain dysfunctions related to the psychology of a patient ranging from substance abuse to psychosis.

Electrophysiological brain signals are typically recorded by an electroencephalogram ("EEG") system. The EEG system may be a device that measures the electrical activity in the brain via a multitude of electrodes attached to a patient's scalp by way of a cap or a special glue or paste and connected to the EEG system through wires, called leads. The electrodes detect the electrophysiological signals, and the EEG system amplifies and records them onto paper or computer for analysis by medical personnel.

Recording the EEG signals allows medical personnel to view information (e.g., a graph) reflecting the activity of thousands of neurons in the brain. The pattern of activity in the recorded EEG signals or brain waves changes with the level of the patient's arousal—if the patient is relaxed, the graph shows many slow, low frequency brain waves; if the patient is excited, the graph shows many fast, high frequency brain waves.

While the brain waves provide useful temporal information regarding the electrical activity of the brain, they do not provide the spatial resolution used for determining the exact location of the recorded activity in the brain. High spatial resolution is often important for the diagnosis and treatment of many brain-related conditions such as localized brain tumors and aneurisms.

Higher spatial resolution may be obtained with the use of other brain imaging technologies, including magnetic resonance imaging ("MRI") and functional MRI ("fMRI"). MRI is a technique that utilizes magnetic and radio frequency ("RF") fields to provide high quality image slices of the brain along with detailed metabolic and anatomical information. Radio waves 10,000-30,000 times stronger than the magnetic field of the earth are transmitted through the patient's body. This affects the patient's hydrogen atoms, forcing the nuclei into a different position. As the nuclei move back into place they send out radio waves of their own. An MRI scanner picks up those radio waves, and a computer converts them into images, based on the location and strength of the incoming waves.

fMRI is a technique for determining which parts of the brain are activated by different types of physical sensation or activity, such as sight, sound or the movement of a patient's fingers. This is achieved by arranging an advanced MRI scanner in a particular way so that the increased blood flow to the activated areas of the brain shows up on the detailed image slices of the brain.

In order to take advantage of the high temporal resolution of EEGs and the high spatial resolution of MRIs and fMRIs, medical personnel have been increasingly performing simultaneous recordings of EEG and MRI or fMRI data for both medical diagnosis and clinical research. Such simultaneous recording provides the high spatio-temporal resolution needed to study brain activity during different tasks, such as visual, auditory, or motor tasks. Currently, there is no single brain imaging technology that can provide the resolution needed to study this brain activity. The combination of EEGs and MRIs/fMRIs provides the needed resolution, while improving the accuracy of diagnosis of many brain-related conditions.

The combination of these two conventional technologies, however, may provide several safety problems. One such problem involves the integrity of the measurements, as the changing magnetic and RF fields of an MRI/fMRI recording can introduce undesirable artifacts into the EEG recordings. When EEG leads are placed inside an MRI scanner, the rapidly changing RF fields may introduce voltages that obscure the EEG signals. Further, the presence of magnetic materials within the EEG electrodes placed inside the MRI scanner and the electromagnetic radiation emitted by the EEG machine can disturb the homogeneity of the magnetic field, and possibly compromise the quality of the MRI image scans.

The introduction of the EEG equipment into the pulsed RF fields created by the MRI scanner can also present a safety hazard, especially at high static $B_0$ fields because of Specific Absorption Rate ("SAR") considerations. EEG leads may act as antennas, increasing the patient's exposure to the RF fields. The use of metallic electrodes and leads may cause an undesirable increase in local and whole-head SAR values, reflected in the heating of patient's tissue. Such heating may possibly result in bodily injury to the patient, including burns, electric shock, etc.

Noise can also be introduced into the EEG signals during EEG recording within an MRI scanner. Specifically, noise may be introduced by motion within the MRI environment during the recording of the EEG signals. This motion noise may be associated with a ballistocardiogram motion, e.g., a cardiac pulsation, within the patient, a movement of the patient during the EEG recording, etc. The amplitude of the noise may be approximately of the same magnitude of the EEG signals. Because these motion noises may be present as a direct result of an electromagnetic induction in the magnetic field, the voltage differential between the amplitude of the noise and the amplitude of the EEG signals can increase as the strength of the magnetic field increases.

Several measures have been previously used to alleviate the problems associated with the concurrent use of an EEG machine and the MRI scanner. One such possibility is to replace conventional electrodes with electrodes composed of non-ferromagnetic materials, such as carbon fiber. For example, in U.S. Pat. No. 6,708,051, entitled "FMRI Compatible Electrode and Electrode Placement Techniques," issued on Mar. 16, 2004, an apparatus for simultaneous EEG/MRI recordings is described as having electrodes and leads that are composed of non-ferromagnetic materials. As described in this U.S. Patent, the electrodes and leads are attached to a stretchable elastic cap fitting the patient's head. It is indicated in this publication that the electrodes and leads provided in the cap may be made of carbon, carbonized plastic or other conductive plastic.

The non-metallic nature of the electrodes and leads makes them less susceptible to induced currents present in the MRI scanner, as well as other artifacts caused by movement of the body within the MRI scanner. However, carbon fibers have a high and fixed conductivity that may not be easily reduced in a cost-effective and commercially feasible manner. The conductivity of the carbon fibers may affect the measurement of the EEG signals. Thus, it is desirable for other materials with lower conductivity to be used as electrodes at least in such arrangement.

Another possibility is to rearrange the EEG equipment leads, so as to connect the electrodes to the EEG recording machine. The placement and alignment of the EEG equipment leads within the MRI scanner can have a substantial impact on the resultant image quality. This is because the EEG leads can interfere with the RF fields within the MRI scanner by de-tuning the coils used in the MRI scanner, thereby resulting in a global attenuation of the received RF signal. For example, U.S. Pat. No. 5,445,162, entitled "Apparatus and Method for Recording an Electroencephalogram During Magnetic Resonance Imaging," issued on Aug. 29, 1995, describes a system which relocates the EEG machine to a remote and isolated location that is external to the MRI scanner room so as to minimize the interference between the two systems.

Similarly, International Publication No. WO 03/073929, entitled "Electroencephalograph Sensor for Use with Magnetic Resonance Imaging and Methods Using Such Arrangements," and published on Sep. 12, 2003, describes an EEG recording system which includes an EEG machine which is external to the MRI environment, and that receives the electrical signals via optical fiber between a transmitter located inside the MRI room and a receiver external to the MRI room.

Yet another possibility to address the problems associated with the concurrent use of EEG and MRI machines, and in particular, the motion and other artifact noise that affect the quality of EEG recordings, is to use a filtering system coupled to motion sensors attached to the patient's scalp. Such a system is described in International Publication No. WO 2004/047632, entitled "Apparatus and Method for Ascertaining and Recording Electrophysiological Signals," and published on Jun. 10, 2004.

While these exemplary measures have assisted in improving the quality of both the EEG and MRI test results, certain problems still exist with such conventional approaches. In particular, there are no methods, systems or arrangements that enable a concurrent recording of that EEG signals and MRI scans, which can simultaneously take into consideration the metallic nature of the electrodes and leads that results in high SAR and RF interferences, the motion and artifact noise within the MRI environment, and the patient safety in general.

Thus, there is a need for methods, systems and arrangements for the delivery and recording of electrophysiological brain signals during MRI that use non-metallic and non-ferromagnetic electrodes and leads.

There is a further need for methods, systems and arrangements to enable delivery and recording of electrophysiological brain signals during MRI that reduce the SAR exposure, while increasing the signal quality and improving patient safety.

There is also a need for methods, systems and arrangements that enable the delivery and recording of electrophysiological brain signals during MRI that reduce the motion and artifact noise within the MRI environment.

SUMMARY OF THE INVENTION

In view of the foregoing, it is one of the objects of the present invention to provide methods, systems and arrangements that enable the delivery and recording of electrophysiological brain signals during MRI that use non-metallic and non-ferromagnetic electrodes and leads.

Another object of the present invention is to provide methods, systems and arrangements that enable a reduction of the SAR exposure while increasing signal quality and improving patient safety.

Still another object of the present invention is to provide methods, systems and arrangements that enable a reduction of the motion and artifact noise within the MRI environment.

These and other objects of the present invention are achieved by exemplary methods, systems and arrangements that achieve lower SAR and higher signal quality and patient safety with the use of e.g., a conductive ink sensor system attached to a conductive ink head cap. The conductive ink sensor system can include a set of particular electrodes, leads and motion sensors specifically designed to reduce the MRI artifact noise, current delivery, and SAR levels.

For example, these electrodes, leads, and motion sensors can be made of conductive inks that are composed of various types of non-ferromagnetic conductive mixtures such as carbon, silver, and silver chloride, among others. The electrode system can be coupled to a conductive ink head cap made of blended silver/carbon microstrips of conductive ink with, e.g., 32 sensor positions according to a 10-20 system of electrode placement. The sensor layout within the system may be optimized to enhance source localization inverse computations, with customizations for particular brain regions and experiment types. In addition, the sensor system may be fully disposable, partially-disposable with full or partial replacement of components, or modular in nature with disposable components.

In one exemplary embodiment of the present invention, the sensor system can be connected to a EEG machine via multi-layered conductive ink leads that are arranged and coupled together to produce a fixed relative position between sensor wires and reference wires. Groups of the sensors may be partitioned into spatial zones, e.g., frontal, occipital, left or right temporal, etc., possibly each provided with an associated fixed relative position layout. By fixing the positions of the leads relative to ground and reference wires, either by layout on flex-circuit or embedding of wire elements within a molded soft-plastic or cloth matrix, environmental noise due to vibrations within the magnetic field may be substantially reduced.

The leads may be multi-layered, and possibly composed of preferably five layers, e.g., (1) foam layer; (2) polyester/nylon layer, (3) conductive ink layer; (4) dielectric layer, and (5) silicone layer. At a bottom section, e.g., in direct contact with the patient, a thick layer of foam can be provided to reduce and dampen mechanical vibrations produced by head motion, body motion, or vibration from pumps, ventilation fans, or other environmental noise sources, and possibly avoid the lead loops that may cause patient burns. In addition, a substrate of polyester, plastic sheets, or any other non-conductive, non-ferromagnetic flexible material may be used as a deposit layer for a conductive ink layer. The conductive ink layer may be coated with purely dielectric inks to primarily insulate the patient from the negative effects of and direct contact with MRI RF coils. The dielectric and optionally the substrate are finally covered with silicone or other biocompatible material.

In another exemplary embodiment of the present invention, the electrodes may be multi-layered, and possibly composed of three layers, e.g., (1) a bottom layer consisting of a female grommet for attaching to the conductive ink cap, (2) a mid layer consisting of an open-ended conductive ink trace extending out of a multi-layered lead, and (3) a top layer consisting of a male grommet and a thin layer of the conductive ink with extrusion points for making contact with an electrode paste.

To further reduce motion and artifact noise in the concurrent EEG/MRI environment, according to still another exemplary embodiment of the present invention, motion sensors may be integrated into the design of the sensor system, e.g., as a part of the cap within which the electrodes are bound, and/or physically connected to all or some of the electrodes.

Additionally, according to a further exemplary embodiment of the present invention, the multi-layered leads may have a variable resistance along the length of individual sensor leads, with a resistance profile dictated by specific frequency response attenuation used for a particular recording application of an anatomical structure. The multi-layered leads may also possess impedance profiles that are configured to particular MRI field strengths or applications with specific pulse sequences with differing RF characteristics. Further customizations may be effectuated to optimize the performance for specific MRI systems and models, specific bore configurations, head coils, and EEG recording systems.

In accordance with another exemplary embodiment of the present invention, the sensor system may be used for current delivery as is the case for in Electrical Impedance Spectrography ("EIS") or Electrical Tomography ("EIT") by pre-configuring an impedance profile for each electrode using an acquisition system software so to adjust impedance measurements. The sensor system may also be used for Transcranial Magnetic Stimulation ("TMS"). Further, the conductive ink cap may be adapted for EEG recordings during FMRI of both human and animal subjects.

Advantageously, the exemplary embodiments of methods, systems and arrangements of the present invention can achieve lower SAR and lower temperature increase as compared to metallic or carbon fiber electrodes and leads, with approximately the same input power. The exemplary embodiment of the sensor system of the present invention may be safely used in high magnetic fields because of the minimal or no use of metals and the very weak interaction with the RF fields generated by the MRI scanner. Additionally, the multi-layered leads of this system may be less susceptible to induced ballistocardiogram currents and the sensors are less susceptible to Eddy currents that can introduce sensor heating and diminish image quality. The resistivity of the leads can also greatly increase the signal-to-noise ratio ("SNR") of the EEG recordings.

BRIEF DESCRIPTION OF THE DRAWINGS

The foregoing and other objects of the present invention will be apparent upon consideration of the following detailed description, taken in conjunction with the accompanying drawings, in which like reference characters refer to like parts throughout, and in which:

FIG. 8A is an exemplary diagram of a middle layer of the electrode and an attached multi-layered lead according to the exemplary embodiments of the present invention;

DETAILED DESCRIPTION

Generally, an exemplary embodiment of the present invention provides methods, systems and arrangements for the delivery and recording of electrophysiological brain signals during MRI. As used herein, electrophysiological brain signals generally refer to signals that record the electrical activity of the brain. These signals may be acquired by an electroencephalogram ("EEG") machine, e.g., a system that can measure an electrical activity in the brain via a multitude of electrodes coupled to a patient's scalp via a cap, glue, or paste, and electrically coupled to the EEG machine via leads. Signals acquired by the EEG machine may be interchangeably referred to herein as electrophysiological brain signals, EEG signals, or brain waves.

Electrodes as used herein may preferably include a conductive medium used to record an electrical signal from a patient. A group of electrodes may be attached to a cap which can fit the patient's head so as to acquire the EEG signals in accordance with the present invention. The electrodes may be attached to the cap according to e.g., a 10-20 system or any other system of electrode placement.

Further aspects of the exemplary embodiment of the present invention enable an integration of motion sensors into the electrodes attached to the cap. Motion sensors as used herein can include sensors capable of identifying movements within a simultaneous EEG/MRI recording, such as patient movement, patient heart beat, noise associated with a blood flow motion within the patient, noise associated with a ballistocardiac motion within the motion, etc. The electrodes and motion sensors may be interchangeably referred to herein as sensors.

I. Exemplary EEG Recording Apparatus Within an MRI Environment

Figure 1:
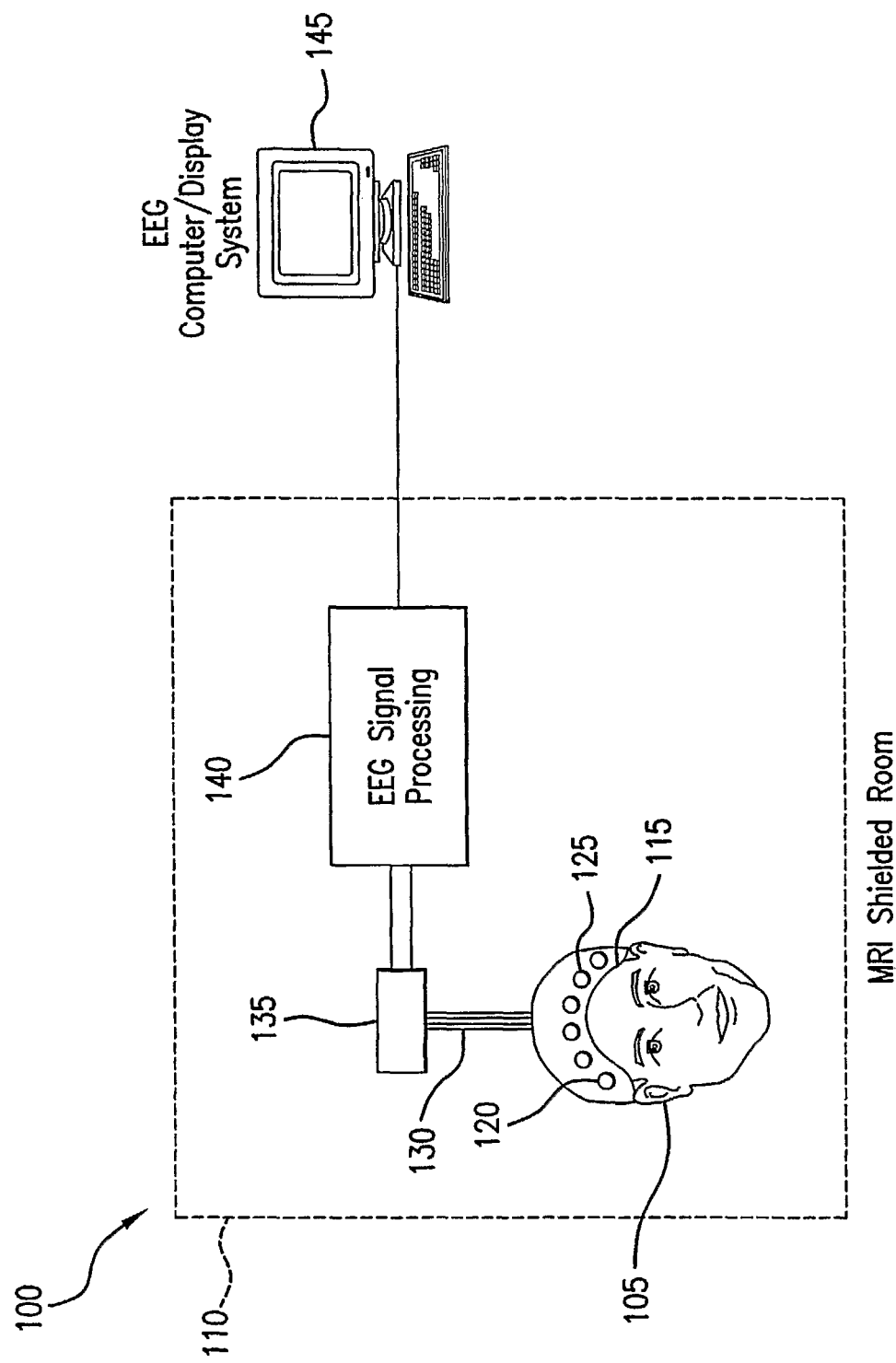
FIG. 1 is an exemplary diagram of an exemplary embodiment of a system for recording EEG signals within an MRI environment according to the present invention.

FIG. 1 shows a diagram of an exemplary embodiment of a system for recording the EEG signals within an MRI environment. The system 100 may be used to record the EEG signals of a patient 105 positioned in an MRI scanner within an MRI-shielded room 110. The system 100 records EEG signals using a cap 115 fitted to the head of the patient 105. As described in further detail hereinbelow, the cap 115 can be a cap made preferably of blended silver/carbon microstrips that include or formed of a conductive ink with multiple (e.g., 32) sensor positions according to a 10-20 electrode placement system.

Attached to the cap 115 are a group of electrodes and motion sensors such as an electrode 120 and a motion sensor 125. The motion sensors may be a part of the cap 115 within which the electrodes are bound, or physically connected to all or some of the electrodes attached to the cap 115. The sensors 120-125 may be attached to the scalp of patient 105 using an electrode paste or glue, such as an EEG paste, as described in further detail hereinbelow.

In accordance with one exemplary embodiment of the present invention, the sensors 120-125 can be made of conductive inks that are composed of various types of non-ferromagnetic conductive mixtures such as carbon, silver, and silver chloride, etc. Further, groups of sensors attached to the cap 115, such as the sensors 120-125, may be partitioned into spatial zones, e.g., frontal, occipital, left or right temporal, etc., each with an associated approximately fixed relative position layout within the cap 115.

The sensors 120-125 can be connected or electronically coupled to EEG signal processing system 140 using multi-layered leads 130 and a connector 135. The multi-layered leads 130 can preferably be formed of five layers as described hereinbelow. The leads 130 may be arranged and bound together in such a way as to produce, e.g., a fixed relative position between sensor wires and reference wires. By fixing the positions of the leads 130 relative to ground and reference wires, e.g., by layout on flex-circuit and/or embedding of wire elements within a molded soft-plastic or cloth matrix, environmental noise due to vibrations within the magnetic field in the MRI-shielded room 110 may be substantially reduced.

The leads 130 may have a variable resistance along the length of individual sensor leads, with a resistance profile likely provided by specific frequency response attenuation used for a particular recording application. The leads 130 may also possess impedance profiles that are configured to specific MRI field strengths or applications, with specific pulse sequences and differing RF characteristics. Further customizations may be made to optimize performance for specific MRI manufacturers and models, specific bore configurations, head coils, and EEG recording systems.

The EEG signals acquired by the sensors within the cap 115 can travel through the leads 130 to an EEG signal processing system 140. The EEG signal processing system 140 may include amplifiers, transmitters, receivers, A/D converters, filters, and any other circuitry or component that may be used to process the acquired signals (e.g., EEG signals) for use and display by an EEG computer and display system 145.

It should be understood by one skilled in the art that the EEG signal processing system 140 or portions of the EEG signal processing system 140 may be located outside of the MRI-shielded room 110. For example, the amplifiers and transmitters may be located inside the MRI-shielded room 110 and connected via optical fiber to the receivers located outside the MRI-shielded room 110. It should also be understood by one skilled in the art that additional circuitry and components may be included in or associated with the system 100, such as electrical stimulators and matrix switches for use in EIS and EIT recordings and adaptive filters for filtering out the noise captured by motion sensors within the cap 115, etc. It should further be understood by one skilled in the art that the EEG computer/display system 145 may execute procedure for processing the EEG signals acquired within the MRI-shielded room 110.

Figure 2:
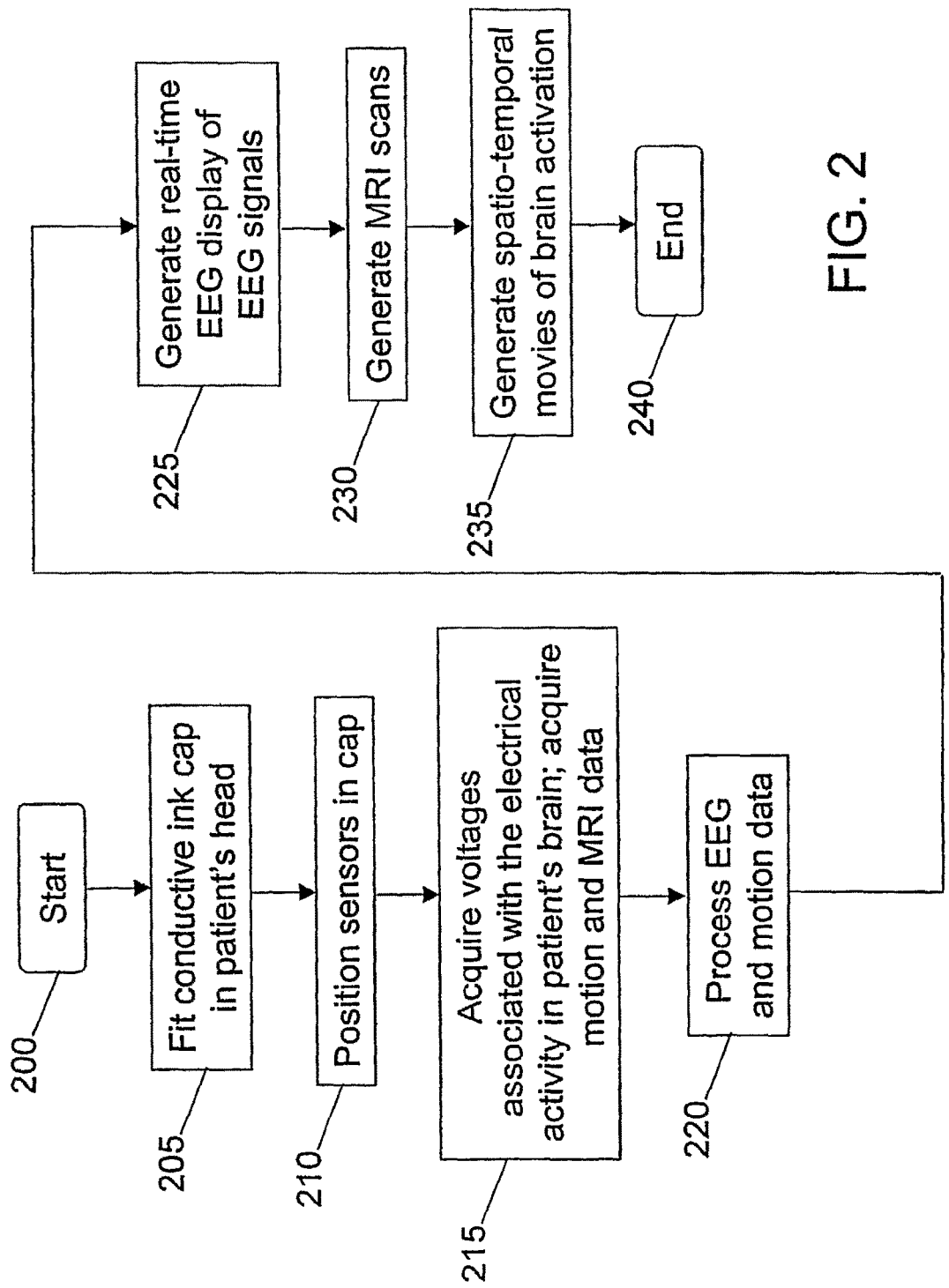
FIG. 2 is an exemplary flow chart of an exemplary embodiment of a method which illustrate exemplary steps for configuring the EEG recording apparatus of the present invention to measure EEG signals during an MRI examination of a patient.

FIG. 2 shows a flow chart illustrating exemplary steps of an exemplary embodiment of the method of the present invention for configuring the EEG recording system of the present invention to measure the EEG signals during the MRI examination of the patient. In step 205 for preparing a patient (such as the patient 105 shown in FIG. 1) to have a concurrent EEG/MRI examination in a MRI-shielded room (such as MRI-shielded room 110 shown in FIG. 1), the conductive ink cap 115 is provided at, on or near the patient's head. The conductive ink cap 115, as described in more detail hereinbelow, can be a stretchable cap made of blended silver/carbon microstrips of conductive ink that may be easily fitted on any patient, both human and animal.

Before, during or after the cap 115 is properly fitted on the patient's head, a sensor system is provided in the cap 115 (step 210). The sensor system may include electrodes for measuring electrophysiological signals for an EEG examination, the motion sensors for measuring any movement present during the patient's concurrent EEG/MRI examination, or any other sensor that may be used to measure brain activity, tasks, or other bodily activity performed by the patient during the examination. As described in more detail hereinbelow, the conductive ink cap 115 may have 32 sensor positions according to the 10-20 or any other number of electrodes arranged by any other system of electrode placement. It should be understood by one skilled in the art that other variations of sensors positioning are possible without deviating from the principles and embodiments of the present invention.

The motion sensors may be integrated into the design of the sensor system, e.g., as a part of the cap within which other sensors (such as the electrodes) are bound, and/or physically connected to all or a fraction of the other sensors in the system. As described above with reference to FIG. 1, the sensor system can be connected to the EEG signal EEG signal processing system 140 using the of leads 130 and the connector 135.

After the arrangement of the sensor system and the leads 130, the patient is positioned in or at the MRI scanner to begin data acquisition for the patient. Thus, the voltages associated with the electrical activity in the patient's brain, motion data, and MRI data can be acquired in step 215. Such voltages may include the EEG signals and other noise signals associated with the patient. The motion data (acquired by the motion sensors) may include noise signals associated with the patient movement, blood flow motion and ballistocardiac motion within the patient, etc.

The EEG and motion data may be processed by the EEG signal processing system 140 in step 220. Such exemplary processing may include, e.g., filtering the acquired signals from noise and motion data, applying the motion data to perform cardiac gating, and any other processing that may be used to generate high SNR EEG signals for a display of the relevant information. The display of the signals acquired during the patient's examination may include a real-time display of the EEG signals (step 225), high quality MRI scans (step 230), and spatio-temporal movies of brain activation formed from the MRI and EEG data (step 235), etc.

It should be understood by one skilled in the art that the exemplary steps shown in the flow chart of FIG. 2 are for illustration purposes only. These exemplary steps may be reordered and/or removed, other steps may be included without deviating from the principles and embodiments of the present invention. For example, the fitting and positioning steps 205-210 may be interchangeable and display steps 225-235 may be reordered or some of them removed. Other steps, such as the steps for generating impedance maps in an EIT examination of the patient, may also be included.

Figure 3:
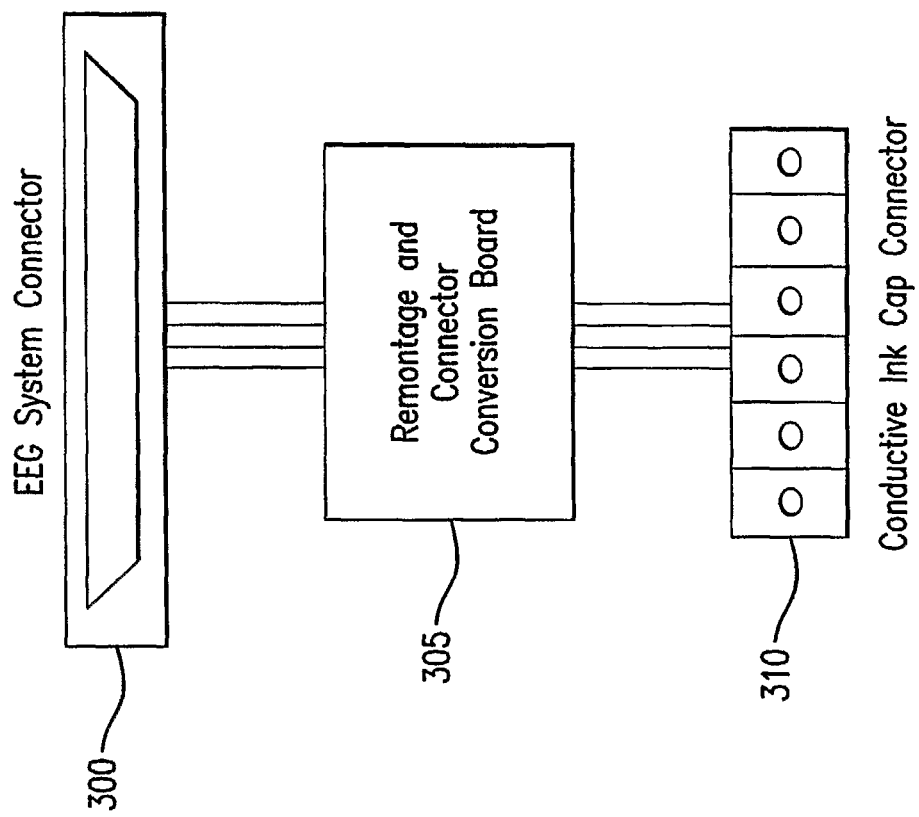
FIG. 3 is an exemplary diagram of an adaptable configuration for use with the exemplary system of the present invention with multiple EEG recording systems.

FIG. 3 shows an exemplary diagram of an exemplary embodiment of an adaptable configuration for use with the exemplary system 100 of the present invention with multiple EEG recording systems. The exemplary system 100 of the present invention for the recording EEG signals concurrently with MRI may be used with the multiple EEG recording systems of various manufacturers by connecting a remontage and connector conversion board 305 between an EEG system connector 300 and a conductive ink cap connector 310:

The EEG system connector 300 may be a connector attached to the EEG signal processing system 140 and/or the EEG computer/display system 145 shown in FIG. 1, or a connector attached to the EEG recording/display system of a particular manufacturer. The conductive ink cap connector 310 can be a connector for the sensors attached to the conductive ink cap 115, as described hereinbelow.

The remontage and connector conversion board 305 can include a number of adaptors for making the conductive ink cap 115 and the sensor system of the present invention compatible with any particular EEG recording system, including an EEG signal processing system, such as the EEG signal processing system 140 shown in FIG. 1, and an EEG computer/display system such as EEG computer/display system 145 shown in FIG. 1. The remontage and connector conversion board 305 may also include a referential or any other bipolar montage for amplifier configuration of the EEG system.

II. Exemplary Conductive Ink Cap

Figure 4:
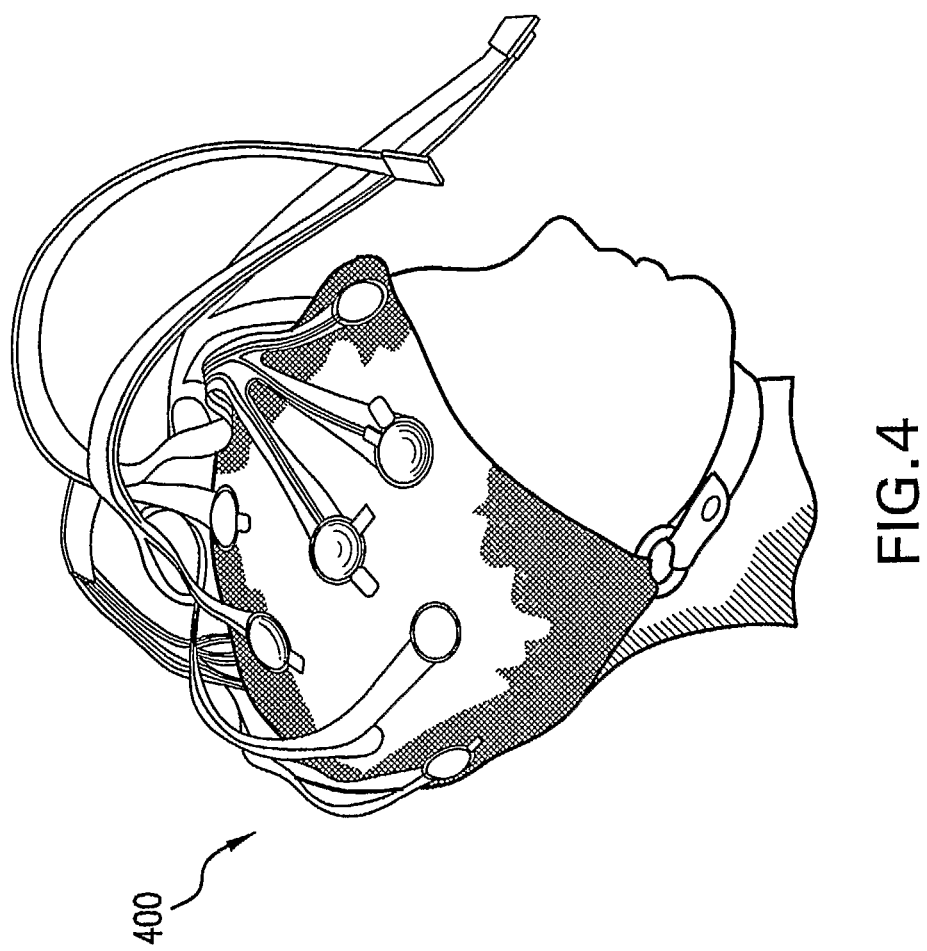
FIG. 4 is an exemplary illustration of a conductive ink cap fitted in a patient head model according to the exemplary embodiments of the present invention.

FIG. 4 shows an exemplary illustration of an exemplary embodiment of a conductive ink cap 400 fitted in a patient head model according to the present invention. The conductive ink cap 400 can be a stretchable cap preferably made of blended silver/carbon microstrips of conductive ink measuring e.g., approximately 750 μm (width) by 125 μm (thick) printed on 125 μm thick polyester (screen printable). For example, the microstrips can be attached to a custom made cap made from Electro-Cap International, Inc., of Eaton, Ohio, with 32 sensor positions according to a 10-20 system of electrode placement.

The conductive ink cap 400 may also be overlaid with an elastic mesh dressing and a tempur-pedic pillow to reduce vibrations. The conductive ink cap 400 may include the industry lightest materials for use on prolonged MRI sessions, and those involving children.

For example, the microstrips' resistivity may be 2 kΩ·m, and their length can vary between 35 and 56 cm. Three microstrips can terminate into two Nicomatic 11506-11 and one Nicomatic 11506-10 connectors with a total of 32 pins. The connectors may be made by Nicomatic, of Bons en Chablais, France. Apart from the sensors attached thereto, the microstrips may be covered with dielectric material and also with a 1.5 mm thick foamy material.

Figure 5A:
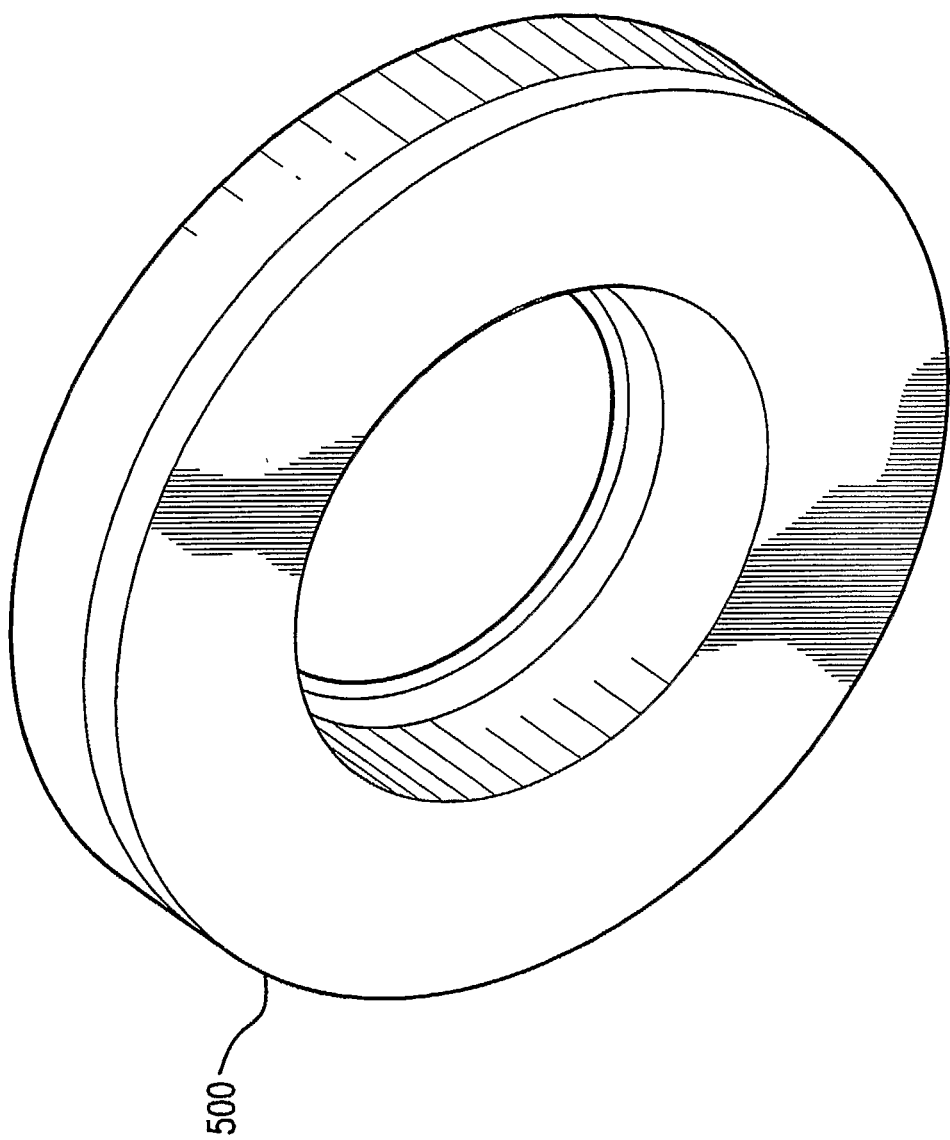
FIG. 5A is an exemplary illustration of a male grommet for attaching a sensor to the conductive ink cap shown in FIG. 4 according to the present invention.
Figure 5B:
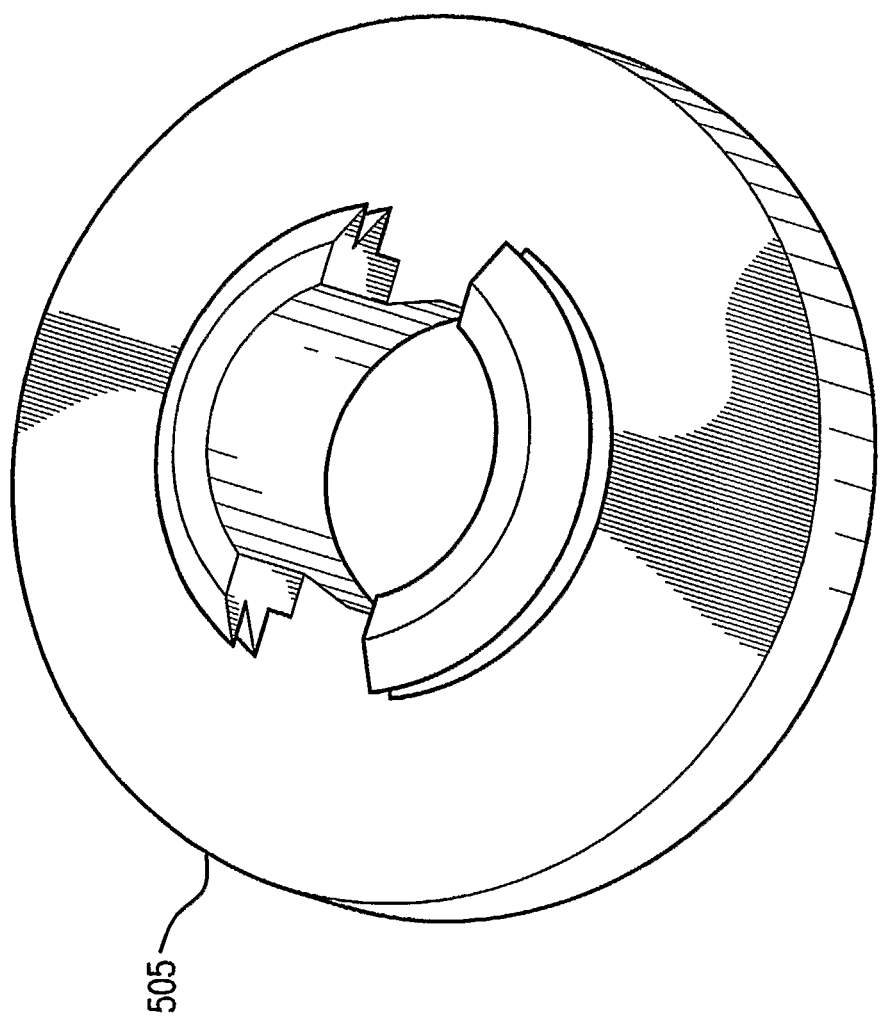
FIG. 5B is an exemplary diagram of a female grommet for attaching a sensor to the conductive ink cap shown in FIG. 4 according to the present invention.

As described in more detail hereinbelow, the sensors can be attached to the conductive ink cap 400 using electrode holders consisting of plastic grommets, such as male grommet KR45GRMM250 (500) and female grommet KR45GRMF250 (505) made by King Richard Canvas & Upholstery, of Andover, Mass., and shown in FIGS. 5A and 5B, respectively. The sensors may be 125 µm thick, and made of printed Ag half-rings with external and internal diameter of 1.6 and 1 cm, respectively. For an electrical contact between the sensor and the electrode paste, a cut conductive disk may be placed over the female grommet 505 shown in FIG. 5B. The conductive disk can be made from Ag and Ag/AgCl inks coated onto a synthetic paper, such as those from Vermed, Inc., of Bellows Falls, Vt.

The sensors may have a low-profile vertical dimension to enhance comfort while the patient is within the MRI head coil bundle. Furthermore, for weight or pressure-bearing sensors, padding may be added to the body of the sensor, or its immediate vicinity to reduce user discomfort. A spatial layout of sensor montages within the sensor system may be optimized to enhance source localization inverse computations, with customizations for particular brain regions and experiment types.

Additionally, connector adapters, such as those that may be parts of the remontage and connector conversion board 305 shown in FIG. 3, may be used to select the application-specific montage or to connect the interface conductive ink cap 400 to EEG systems of different vendors. A connector-saver may also be used to reduce wear on the acquisition system connector parts.

III. Exemplary Conductive Ink Sensor System

Figure 6:
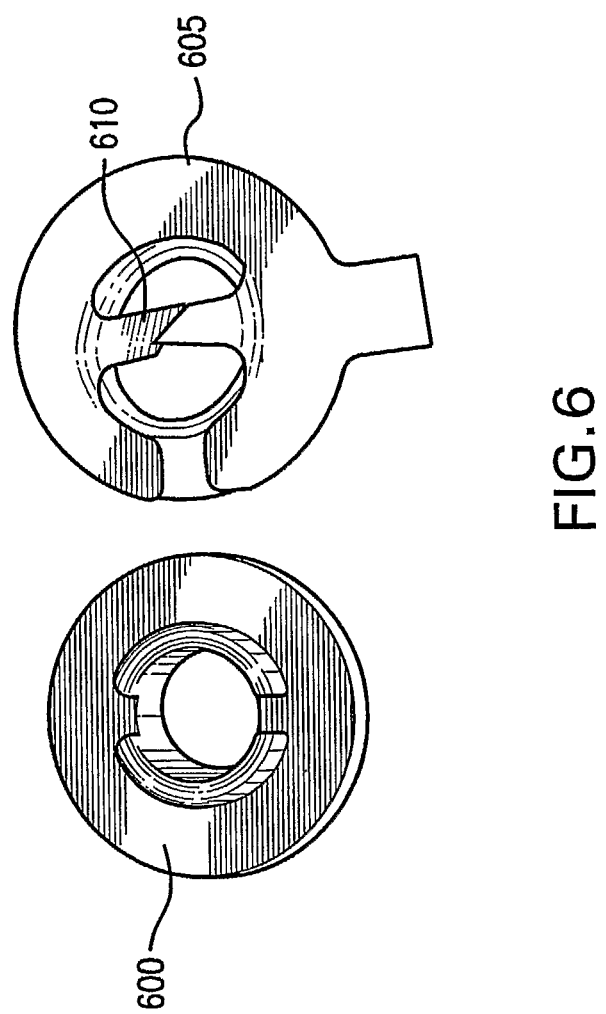
FIG. 6 is an exemplary illustration of the female grommet and male grommet with conductive traces for forming an electrode in accordance with the exemplary embodiments of the present invention.

FIG. 6 shows an exemplary illustration of an exemplary embodiment of a female grommet 600 and a male grommet 605 with conductive traces for forming an electrode in accordance with the exemplary embodiments of the present invention. The female grommet 600 can be attached to a conductive ink cap, such as the conductive ink 400 shown in FIG. 4, as the bottom layer of an electrode. The top layer can be partly formed by the male grommet 605, shown with e.g., a very thin layer of the conductive ink to reduce Eddy currents that may effectuate sensor heating, and diminish image quality. The conductive ink layer can have extrusion points 610 for making contact with the EEG paste, as described hereinbelow.

Figure 7:
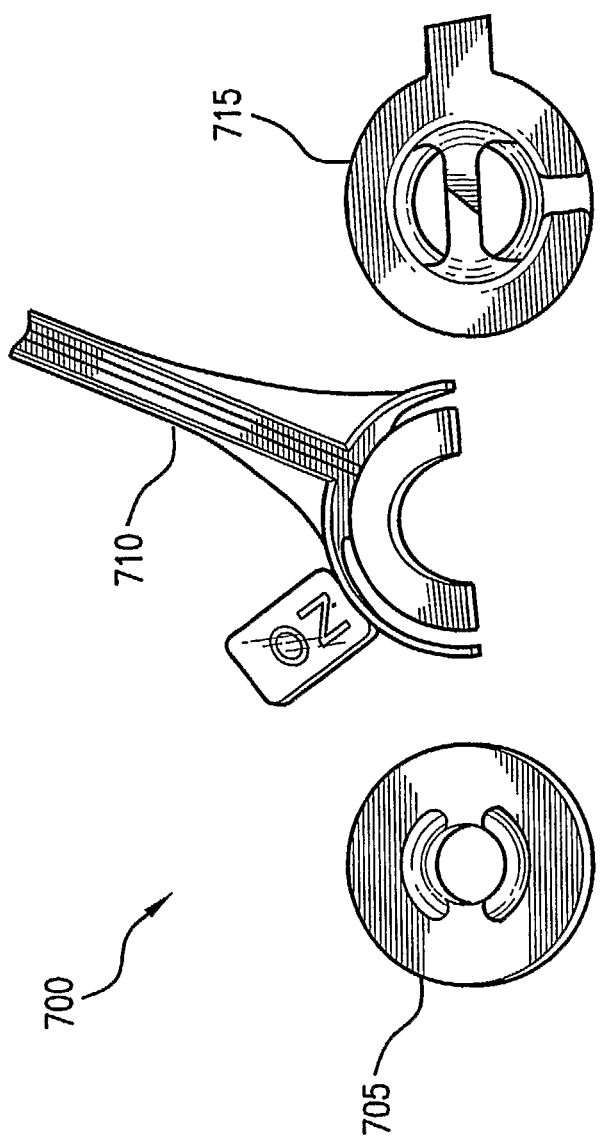
FIG. 7 is an exemplary illustration of a multi-layered electrode according to the exemplary embodiments of the present invention.

FIG. 7 shows an exemplary illustration of an exemplary embodiment of a multi-layered electrode 700 according to the exemplary embodiments of the present invention. The electrode 700 can be composed of three layers, e.g., (1) a bottom layer 705 consisting of the female grommet for attaching to the conductive ink cap, such as the conductive ink cap 400 shown in FIG. 4; (2) a mid layer 710 consisting of a an open-ended conductive ink trace attached to a multi-layered lead; and (3) a top layer 715 consisting of the male grommet with a thin layer of conductive ink and extrusion points for making contact with the electrode paste. The conductive mid and top layers must be open-ended so as not to form a loop through which eddy currents from MRI magnetic field gradients or RF pulses for example could flow.

The exemplary embodiment of a process for joining the three layers for forming an electrode and attaching it to a conductive ink cap according to the present invention is illustrated in FIGS. 9-12 as described herein below.

FIG. 8A shows an exemplary diagram of the middle layer 710 of the electrode and an attached multi-layered lead according to the exemplary embodiments of the present invention. The middle layer 710 can preferably be formed with an open-ended conductive ink trace 805 made of silver chloride, and attached to a multi-layered lead. The multi-layered lead can have a conductive ink trace 800 forming its main conductive layer. The conductive ink trace 800 can be made with a combination of silver and carbon. It should be understood by one skilled in the art that the conductive ink trace 805 may extend from the conductive ink trace 800, as shown in FIG. 8A.

Figure 8B:
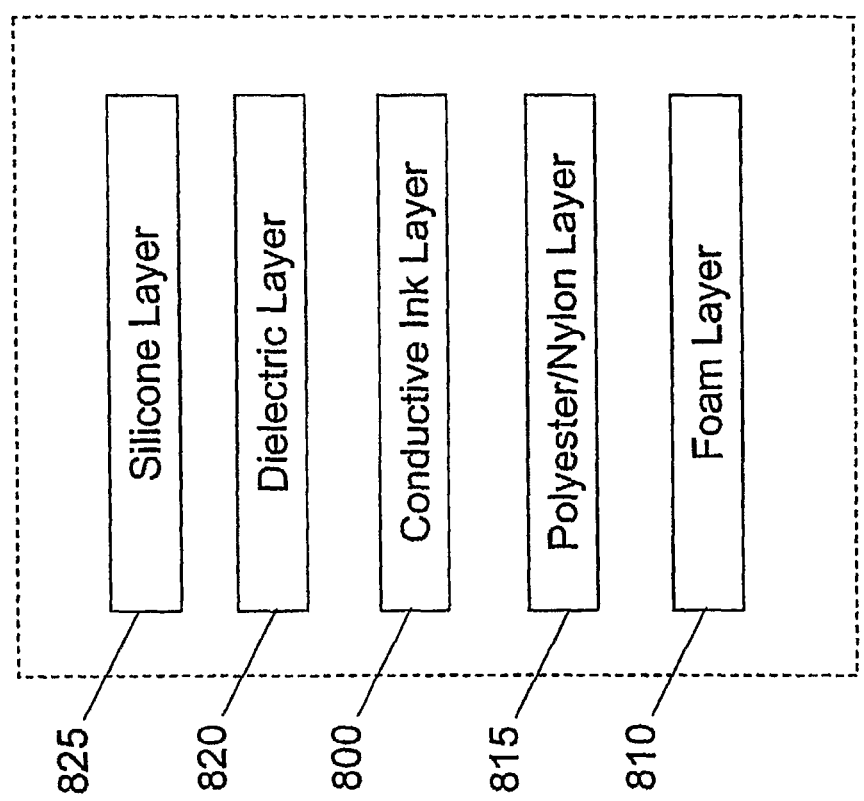
FIG. 8B is an exemplary block diagram of the exemplary layers of materials used to form the multi-layered lead shown in FIG. 8A.

FIG. 8B shows an exemplary block diagram of the exemplary layers of materials that can be used to form the multi-layered lead shown in FIG. 8A. A multi-layered lead can be made of, e.g., five (5) layers of materials: (1) foam layer 810, (2) polyester/nylon layer 815, (3) conductive ink layer 800, (4) dielectric layer 820, and (5) silicone layer 825. At the bottom of the arrangement, in preferably direct contact with the patient, a thick layer 810 of foam is provided to reduce and dampen mechanical vibrations produced by head motion, body motion, or vibration from pumps, ventilation fans, or other environmental noise sources, and avoid the lead loops that may cause patient burns. Next, a substrate of polyester, plastic sheets, or any other non-conductive, non-ferromagnetic flexible material is provided as a deposit layer (the layer 815) for the conductive ink trace 800.

The conductive ink trace 800 can then be coated with purely dielectric inks in the dielectric layer 820 to primarily insulate the patient from MRI RF coils. The dielectric and optionally the substrate can be covered with silicone or other biocompatible material in a silicone layer 825. Table I below shows exemplary the substances that may be used to form a lead according to the principles and embodiments of the present invention.

TABLE I

Substances for Forming a Conductive Ink Lead

| Pigment | Carrier | Substrate | Binder | Typical Resistivity |
|---|---|---|---|---|
| Ag, Ag/Cl, C, Au, doped Si, Translucent resistive polymer thick film, etc. | $H_2O$, solvent | Polyester paper, etc. | Vinyl, Nitrocellulose, Acrylic Urethane, Thermoplastic, etc. | 2-3 k$\Omega$•m |

It should be understood by one skilled in the art that some of the layers for forming a lead may be omitted or modified without deviating from the principles and embodiments of the present invention.

Figure 9:
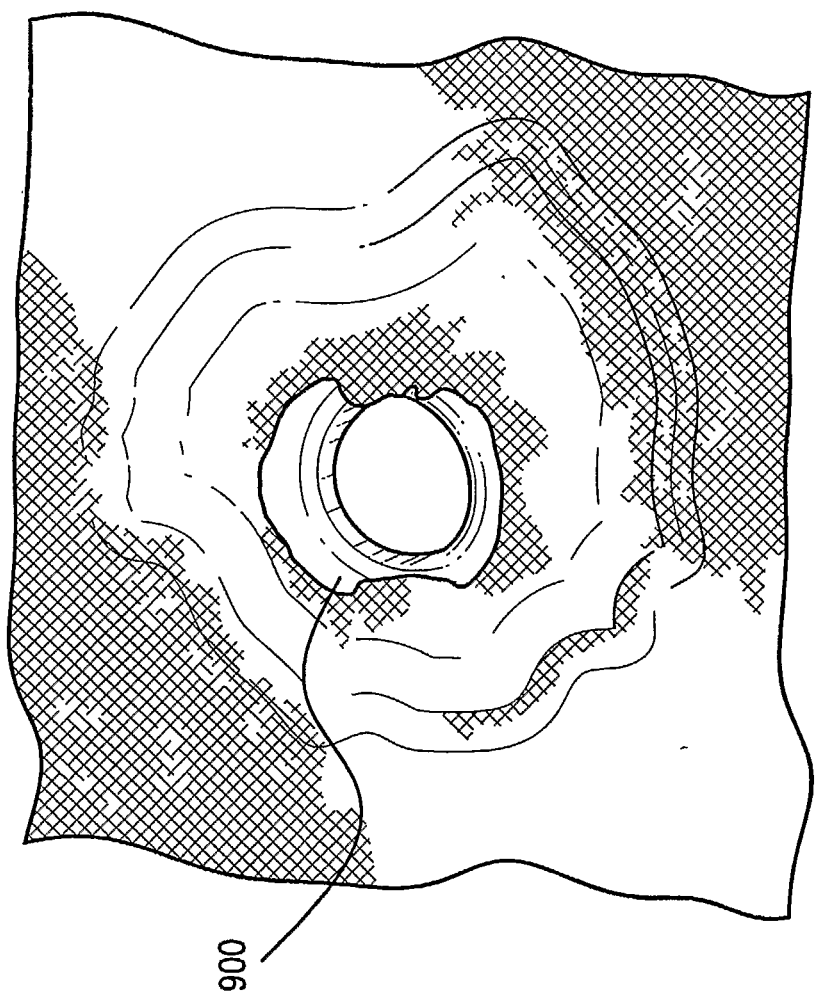
FIG. 9 is an exemplary illustration of the female grommet configured to be attached to the conductive ink cap according to the present invention.

FIG. 9 shows an exemplary illustration of an exemplary embodiment of a female grommet 900 attached to a conductive ink cap. As shown in FIG. 9, the female grommet 900 is attached under the conductive ink cap for forming the bottom layer of an electrode.

Figure 10:
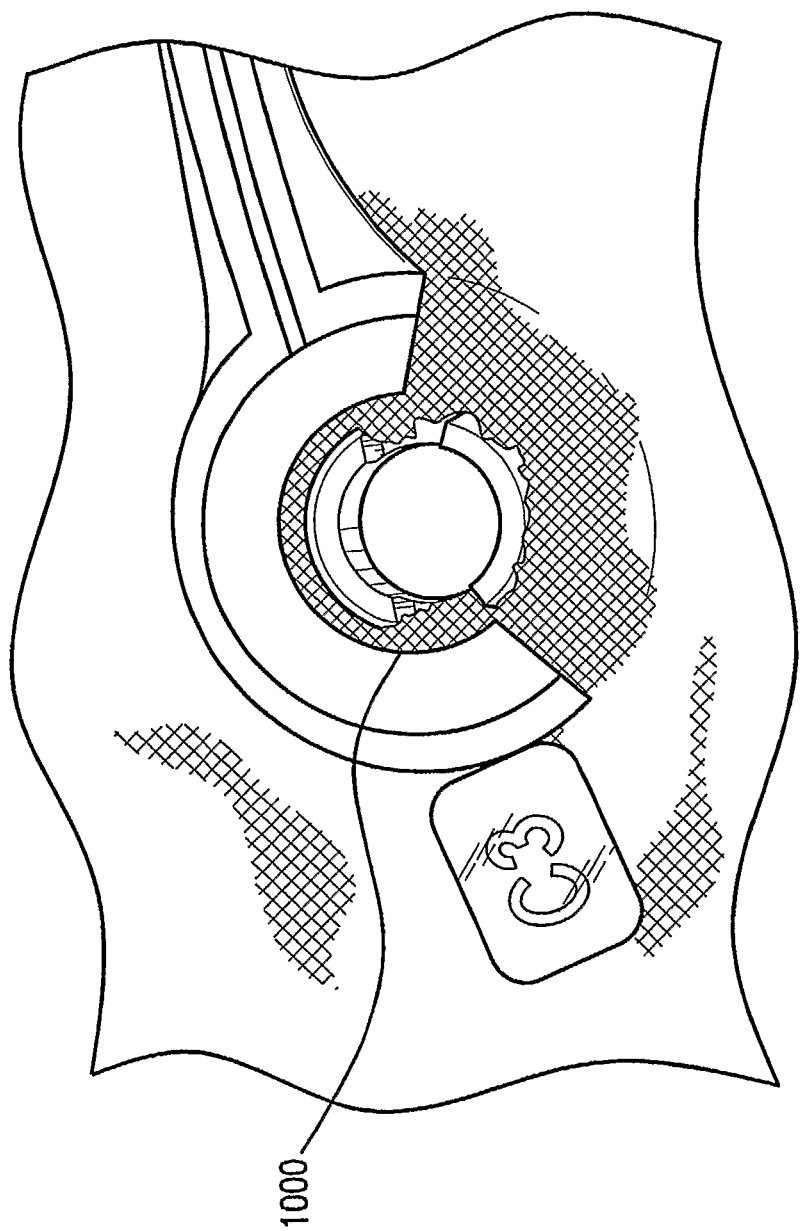
FIG. 10 is an exemplary illustration of the mid-layer of the electrode connected to its bottom layer and attached to a conductive ink cap according to the present invention.

FIG. 10 shows an exemplary illustration of an exemplary embodiment of a mid-layer of an electrode connected to its bottom layer, and attached to the conductive ink cap. The mid-layer 1000 can be formed of an open-ended conductive ink trace attached to a multi-layered lead, and positioned on top of the bottom layer 900 (see FIG. 9).

Figure 11:
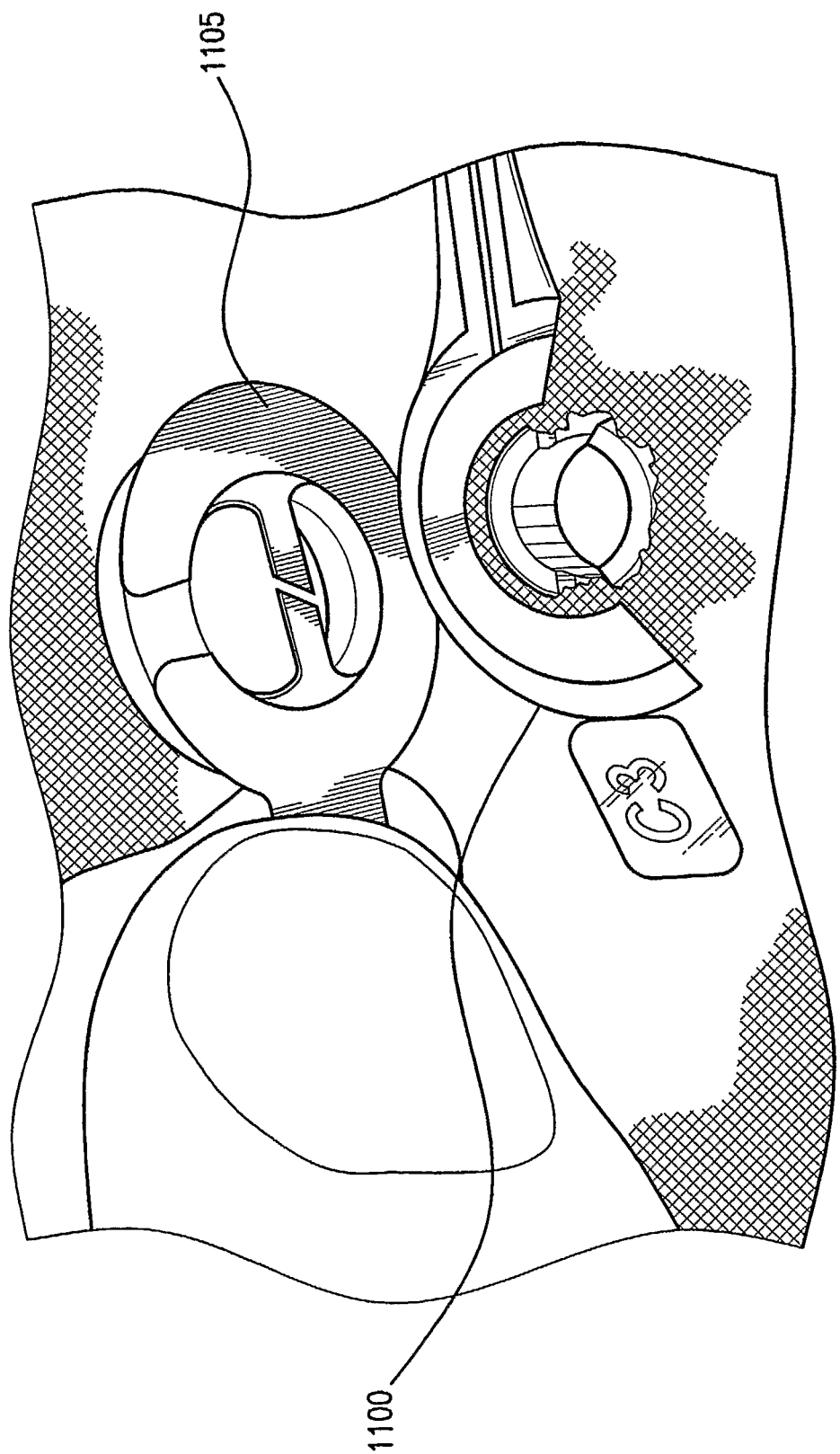
FIG. 11 is an exemplary illustration of the top layer of the electrode connected to its mid and bottom layers according to the present invention.

FIG. 11 shows an exemplary illustration of an exemplary embodiment of a top layer 1105 of an electrode connecting to its mid and bottom layers. The top layer 1105 is shown connecting to a mid-layer 1100, which is positioned on top of the bottom layer 900 (see FIG. 9). Both the top layer 1105 and the mid-layer 1100 can be formed of the conductive inks, as described hereinabove.

Figure 12:
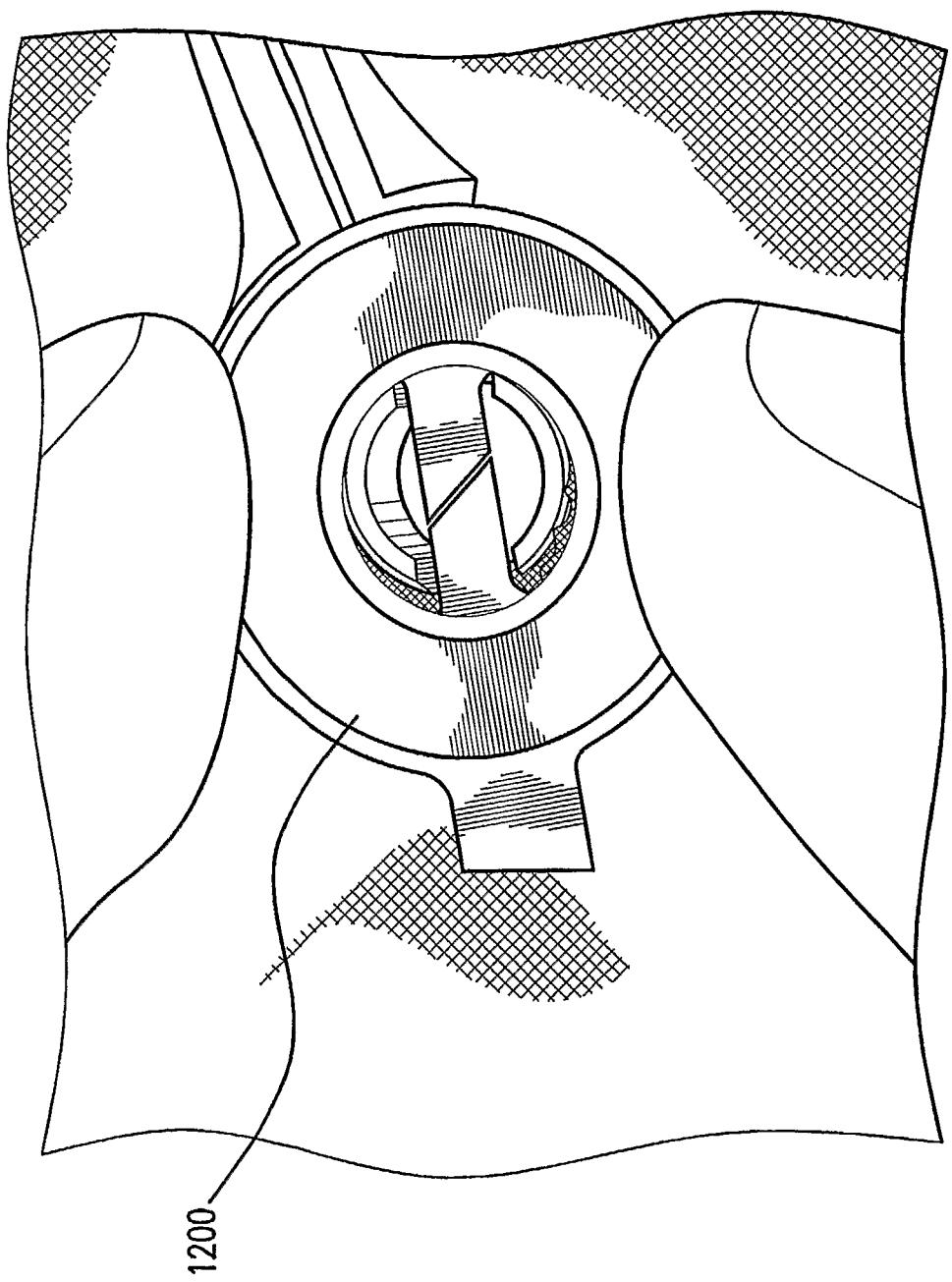
FIG. 12 is an exemplary illustration of the exemplary electrode attached to a conductive ink cap according to the present invention.

FIG. 12 shows an exemplary illustration of an exemplary embodiment of an electrode 1200 attached to the conductive ink cap. Following the illustrated procedure for in FIGS. 9-11, the electrode 1200 can be formed. The electrode 1200 may be formed of three layers, such as the top layer 1105 and the mid-layer 1100 (see FIG. 11) and the bottom layer 900 (see FIG. 9).

Figure 13:
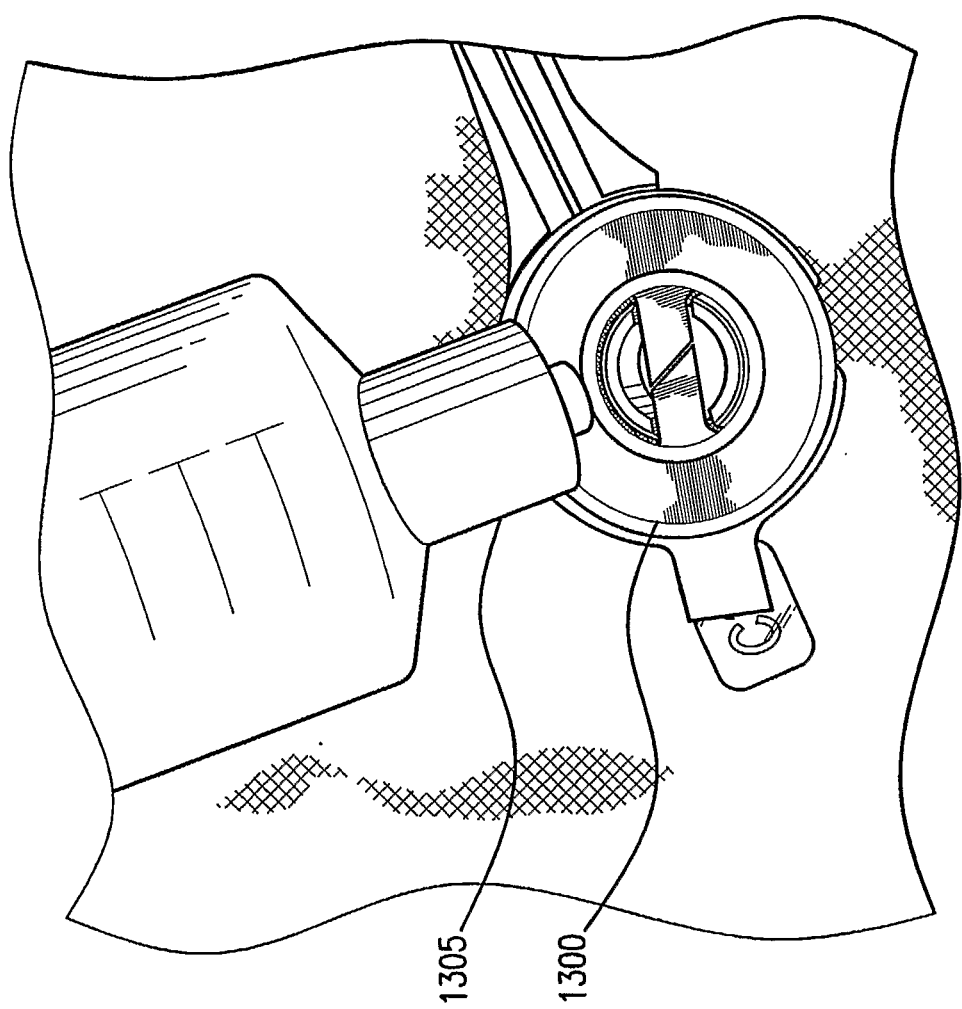
FIG. 13 is an exemplary illustration of the EEG paste being deposited on the electrode attached to a conductive ink cap according to the present invention.

With the electrode 1200 in place, the next step is to use a EEG paste 1305 for making contact between the electrode 1200 and the patient's scalp, as shown in FIG. 13.

The EEG paste 1305 is deposited on the electrode 1300 for forming contact between the conductive ink extrusions of the top layer 1105 (FIG. 11), the open-ended conductive ink trace attached to the multi-layered lead forming mid-layer 1100 (see FIG. 11), and the patient's scalp.

Figure 14:
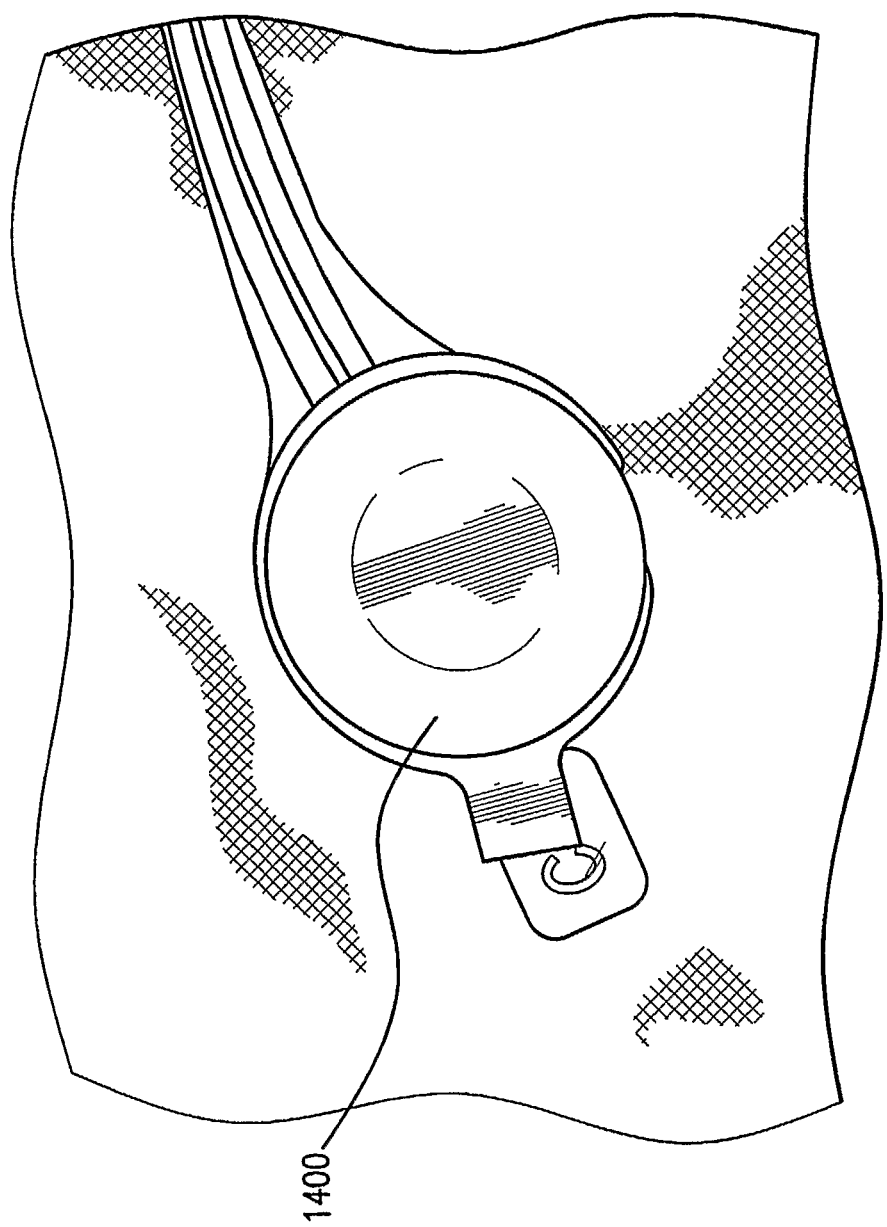
FIG. 14 is an exemplary illustration of the electrode filled with the EEG paste for the recording of EEG signals from a patient.

FIG. 14 shows an exemplary illustration of an exemplary embodiment of an electrode 1400 filled with the EEG 1305 paste for the recording of EEG signals from a patient. The electrode 1400 can be filled with the EEG paste 1305 (see FIG. 13) and attached to the conductive ink cap, such as the conductive ink cap 400 shown in FIG. 4.

Figure 15:
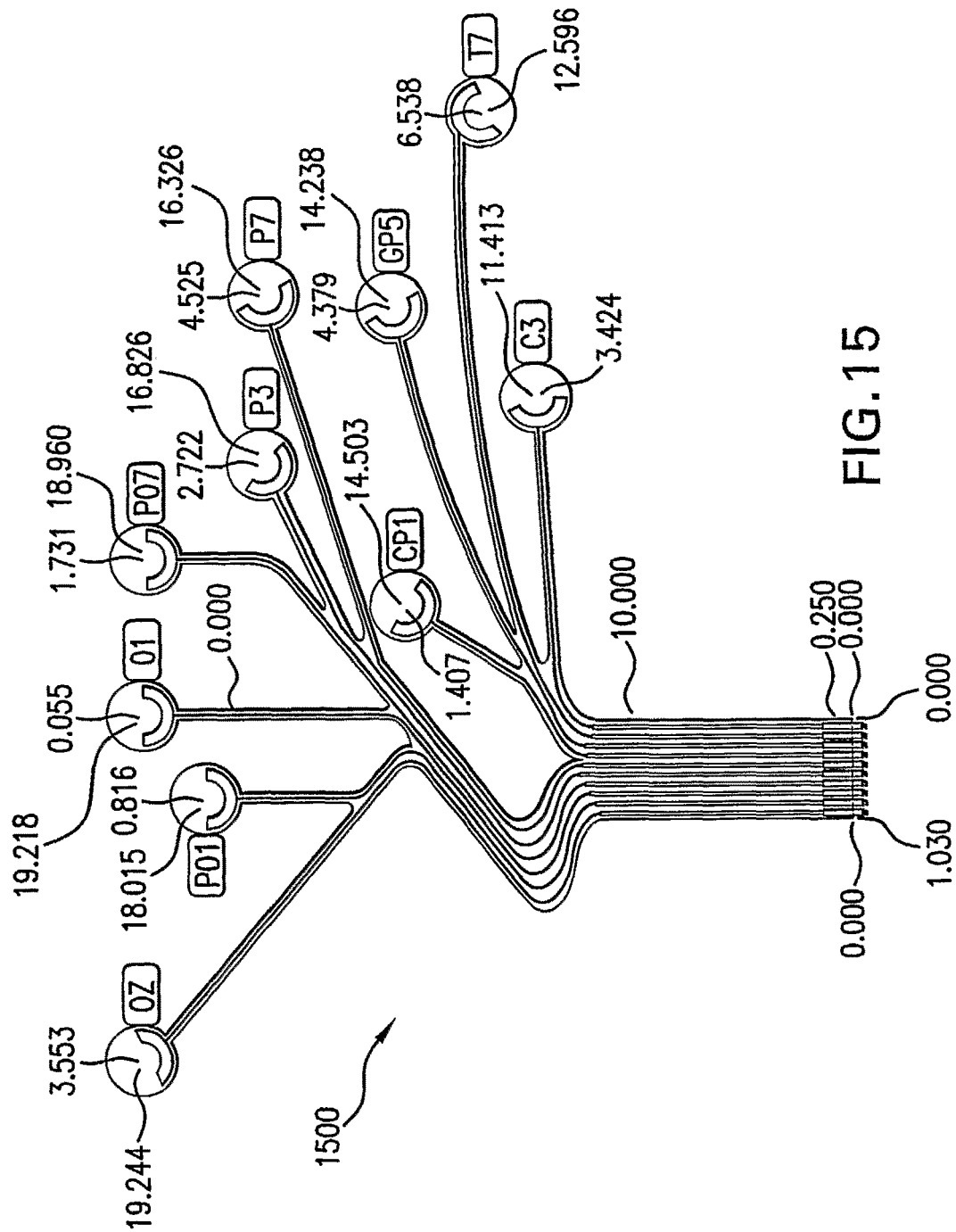
FIG. 15 is an exemplary schematic diagram of a right-side portion of the exemplary embodiment of the sensor system for integration into the conductive ink cap according to the exemplary embodiments of the present invention.
Figure 16:
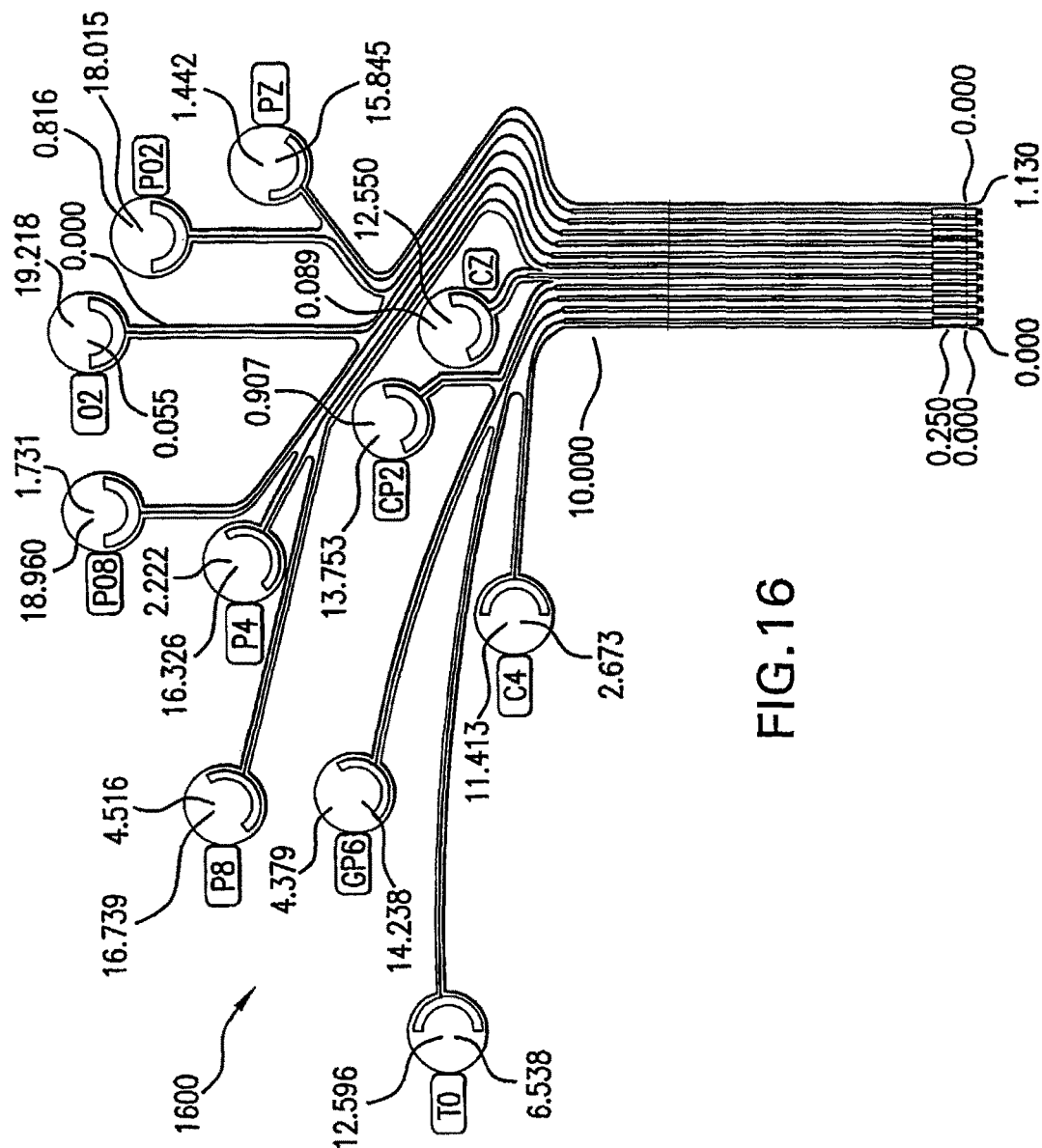
FIG. 16 is an exemplary schematic diagram of a back-side portion of the exemplary embodiment of the sensor system for integration into the conductive ink cap according to the exemplary embodiments of the present invention.
Figure 17:
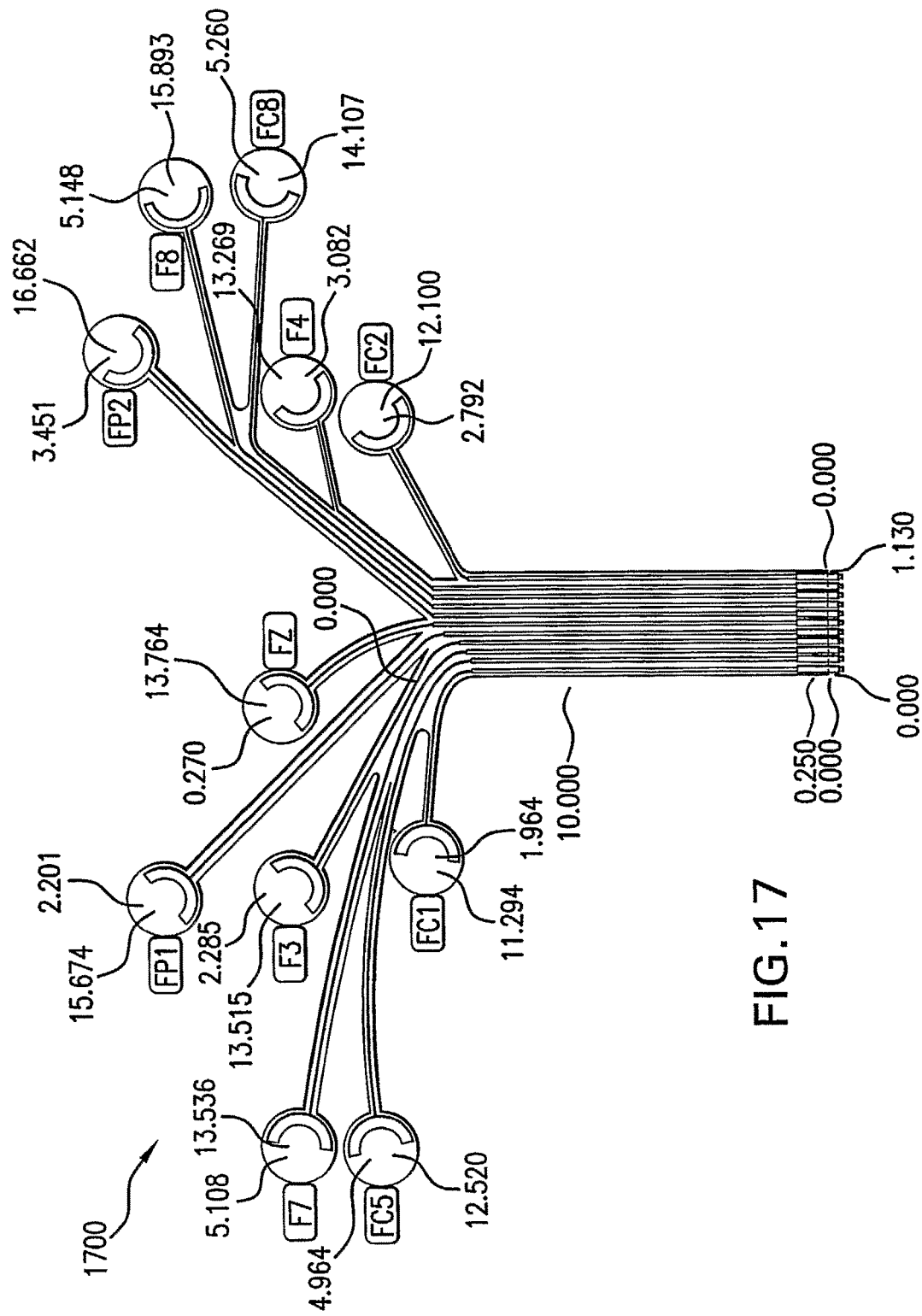
FIG. 17 is an exemplary schematic diagram of a top-side frontal portion of the exemplary embodiment of the sensor system for integration into the conductive ink cap according to the exemplary embodiments of the present invention.

As described hereinabove, the conductive ink cap 400 can be composed of 32 sensor positions, but can also feature a different number of electrodes as required for a particular application. Referring now to FIGS. 15-17, exemplary schematic diagrams of exemplary embodiments of a sensor system for integration into the conductive ink cap are described. The sensor system can be formed by a number of sensors, with, e.g., 10 sensors attached to the right side of the patient's head (see FIG. 15), 11 sensors attached to the back portion of the patient's head (see FIG. 16), and 11 sensors attached to the top frontal portion of the patient's head (see FIG. 17).

As illustrated in FIGS. 15-17, the leads can extend from the sensors for transmitting the EEG signals to the EEG processing system, such as the EEG processing system 140 shown in FIG. 1. The leads can have variable-resistance along the length of individual lead wires, with a resistance profile configured based on by a specific frequency response attenuation used for a particular recording application. The leads may also possess impedance profiles that can be tailored to specific MRI field strengths or applications with specific pulse sequences with differing RF characteristics. Further customizations may be implemented to optimize the performance for specific MRI manufacturers and models, specific bore configurations, head coils, and EEG recording systems.

The leads may be produced with carbon flex-circuit printing, silver flex-circuit printing, carbon-silver composite flex-circuit printing, or variable resistance carbon weave wires. In one exemplary embodiment, the conductive ink layer of the lead can be formed from a resistive lead tapered stripline, as described in Bonmassar, G., "Resistive Tapered Stripline (RTS) in Electroencephalogram Recordings During MRI," IEEE Transactions on Microwave Theory and Techniques, vol. 52, No. 8, pp. 1992-98, August 2004.

Figure 18:
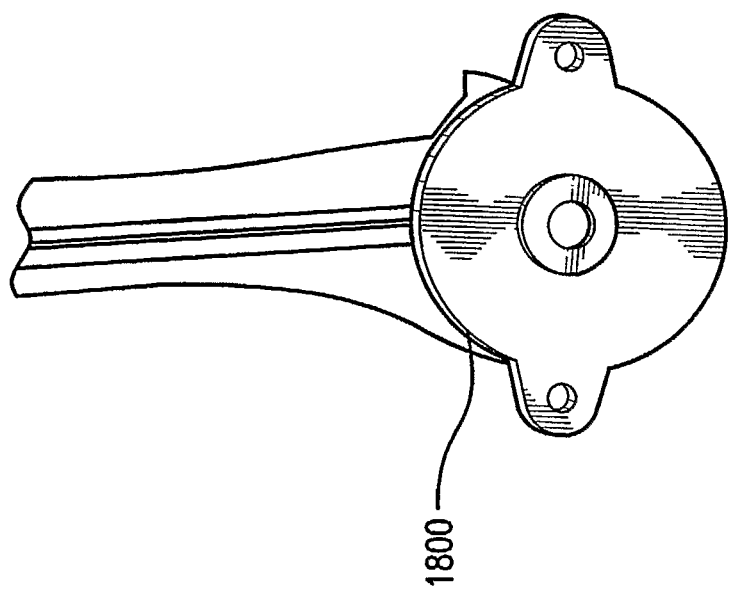
FIG. 18 is an exemplary illustration of a motion sensor in accordance with the exemplary embodiments of the present invention.

FIG. 18 shows an exemplary illustration of an exemplary embodiment of a motion sensor 1800 in accordance with the exemplary embodiments of the present invention is described. The motion sensor 1800 may be integrated into the design of the sensor system, either as a part of the cap within which electrodes are bound, and/or physically connected to all or a fraction of the electrodes in the sensor system. The motion sensor 1800 may include, but is not limited to, inductors, optical motion sensors, piezo-electric elements, micro-electro mechanical accelerometers, or other motion sensing elements. The motion sensor 1800 may be positioned near the temporal artery, e.g., for a maximum detection of the ballistocardiogram artifact, and may have other auxiliary positions throughout the cap, including integration into all or some of the individual electrodes. The motion sensor 1800 may also be configured and used for an MRI cardiac gating.

Additionally, the motion sensor 1800 may be attached to one side to a foam material, such as a tempur-pedic material (opposite to the patient), and placed inside the conductive ink cap (e.g., in the proximity of the temporal arteries to increase motion sensitivity by applying greater contact pressure with the patient's head and to reduce mechanical dampness). The motion sensor 1800 may also be used for filtering the noise on the EEG generated by the magnetic field of the MRI, as described in International Publication No. WO 03/073929, entitled "Electroencephalograph Sensor for Use with Magnetic Resonance Imaging and Methods Using Such Arrangements," and published on Sep. 12, 2003.

IV. Overall Performance of the EEG Recording Apparatus

Figure 19:
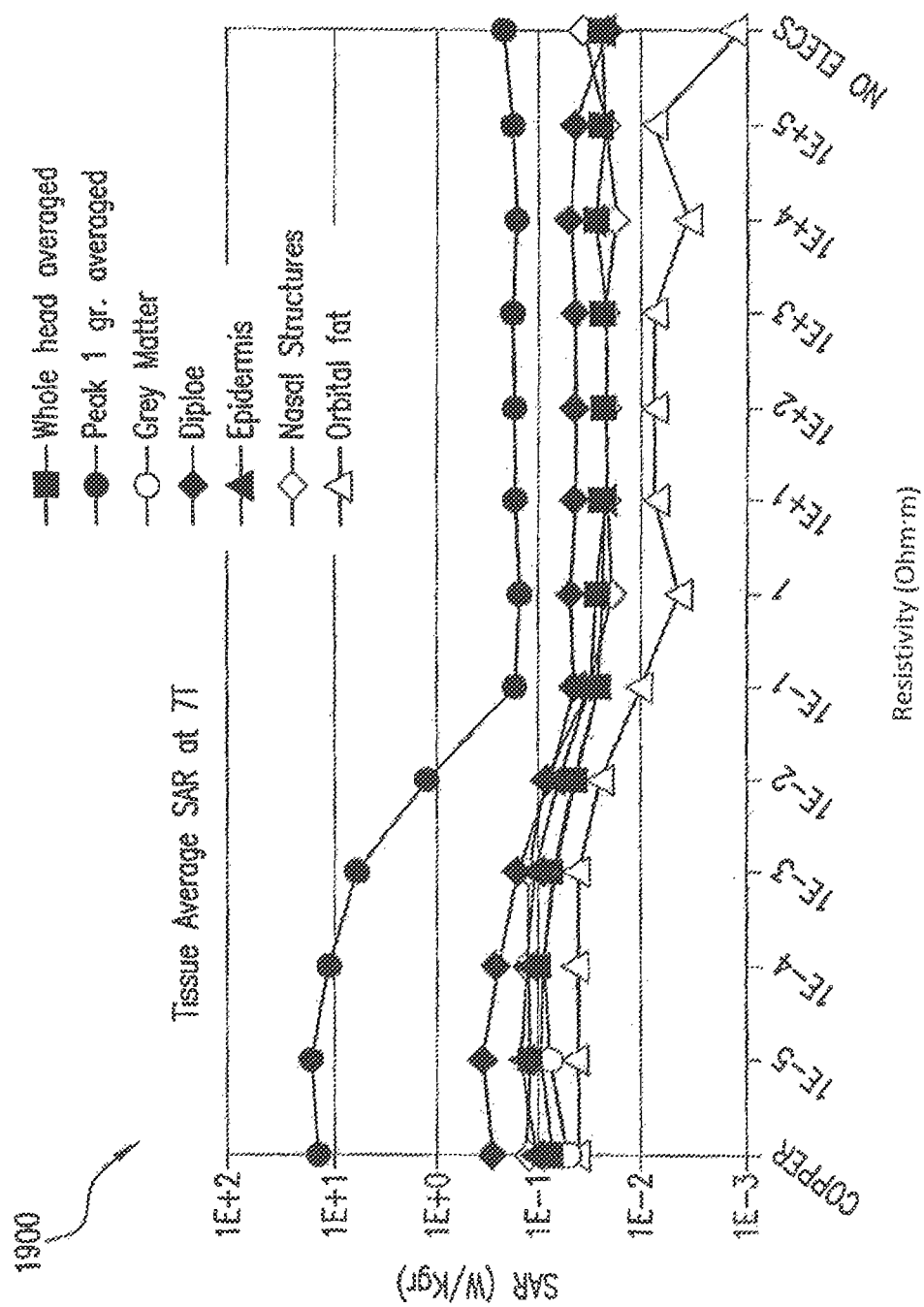
FIG. 19 is a plot of an exemplary peak one gram and tissue average SAR on a 29-tissue head model for various resistivity values of the conductive ink cap's microstrips in a log-log scale.

FIG. 19 shows an exemplary plot 1900 peak one gradient and tissue average SAR on a 29-tissue head model for various resistivity values of the conductive ink cap's microstrips in a log-log scale obtained for the exemplary embodiments of the present invention. The resistivity of the conductive ink cap's microstrips was chosen in accordance with simulation results on a high resolution ($1\times1\times1$ mm$^3$) 29-tissue human head model. The XFDTD program based on the finite-difference time-domain ("FDTD") algorithm and provided by REMCOM Co., of State College, Pa., was used to estimate the electric and magnetic fields and SAR values for different resistivity of the microstrips. All simulations were performed at the RF frequency of 300 MHz corresponding to a $B_0$ of 7 T.

The plot 1900 shows, for a wide range of microstrip resistivities, whole-head averaged and peak 1 gr. averaged SAR and averaged SAR values for several head tissues. Plot 1900 only shows the top five tissues that exhibited the largest SAR increases. As illustrated in the plot 1900, resistivities higher than 0.1 $\Omega\cdot$m correspond to smallest averaged SAR values. The resistivity value selected for the conductive ink cap 400 shown in FIG. 4 (2 $\Omega\cdot$m) was four orders of magnitude larger than a threshold value of 0.1 $\Omega\cdot$m. This figure indicates that the higher resistivity values, achievable with the proposed conductive ink systems but not with other leads, for example, can limit the SAR increases due to electrodes and leads placed on the scalp.

Figure 20:
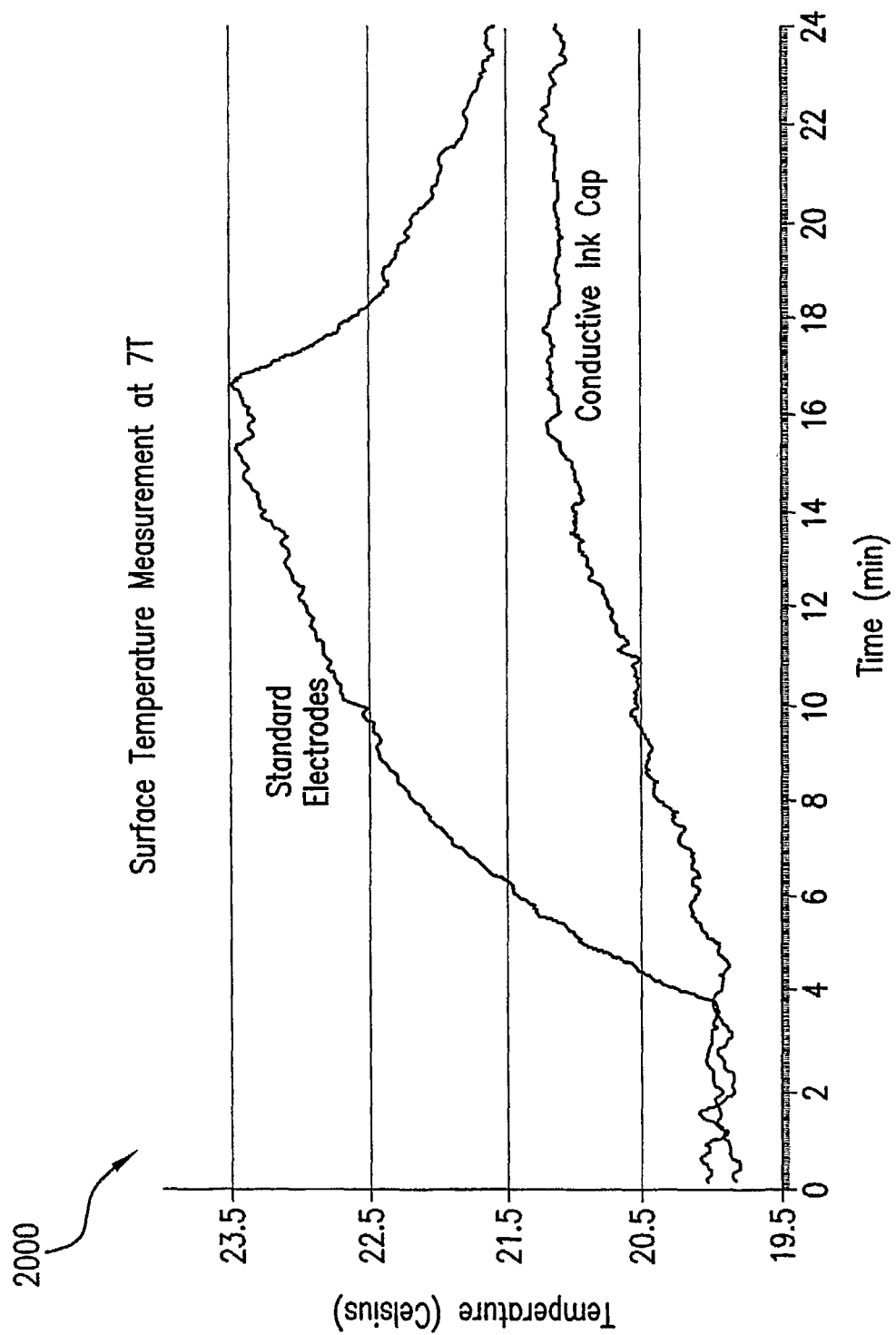
FIG. 20 is a plot of exemplary temperature measurements over time for a head model with standard electrodes and with the conductive ink cap according to the exemplary embodiments of the present invention.

FIG. 20 shows an exemplary plot 2000 of temperature measurements over time for a head model with standard electrodes and with the conductive ink cap according with the exemplary embodiments of the present invention. The temperature measurements were made using a Siemens Allegra 3T head-only system made by Siemens AG of Berlin, Germany, and a custom made 7T whole body system retrofitted with a Siemens console made by Siemens AG of Berlin, Germany. Measurements were performed on a 14 cm diameter solid stand-alone single tissue phantom (1.8 liters of $H_2O$, 42 gr. of Agarose composite hydrogel and 3.6 gr of NaCl) using: (1) the conductive ink cap 400 shown in FIG. 4; (2) the standard low resistive disc electrodes (Gold GRASS F-E5 GH, resistivity 0.66 $\Omega \cdot m$); and (3) no electrodes.

The temperature measurements were performed using a Luxtron 3100 Fluoroptic Thermometer made by Luxtron Corp. of Santa Clara, Calif., with two MRI compatible sensor probes. The temperature values were recorded from the instrument via a serial port to a laptop (9600 Bit/s) and data was filtered with a 10 sec rectangular moving average window. One probe was placed at about 7 cm inside the phantom and the other one at about 4 mm inside the surface. Measurements were reported for the electrode with the highest temperature increase using a high-power T2-weighted turbo spin-echo sequence at 3 T (T2-TSE sequence for 20 minutes, 0.1 W/kg Whole body SAR)) and at 7 T (T2-TSE sequence, 0.6 W/kg Whole body SAR for 15 min).

The plot 2000 shows the temperature measurement results at 7 T. The temperature of the phantom near the electrode in PO7 (see the 10-20 standard montage) peaks at a value three (3) times larger using the standard gold electrodes compared to the use of the conductive ink cap. In a similar experiment done at 3 T, the temperature peak after 20 minutes was 2.4° C. in the standard electrode set and 0.8° C. in the conductive ink cap.

Figure 21:
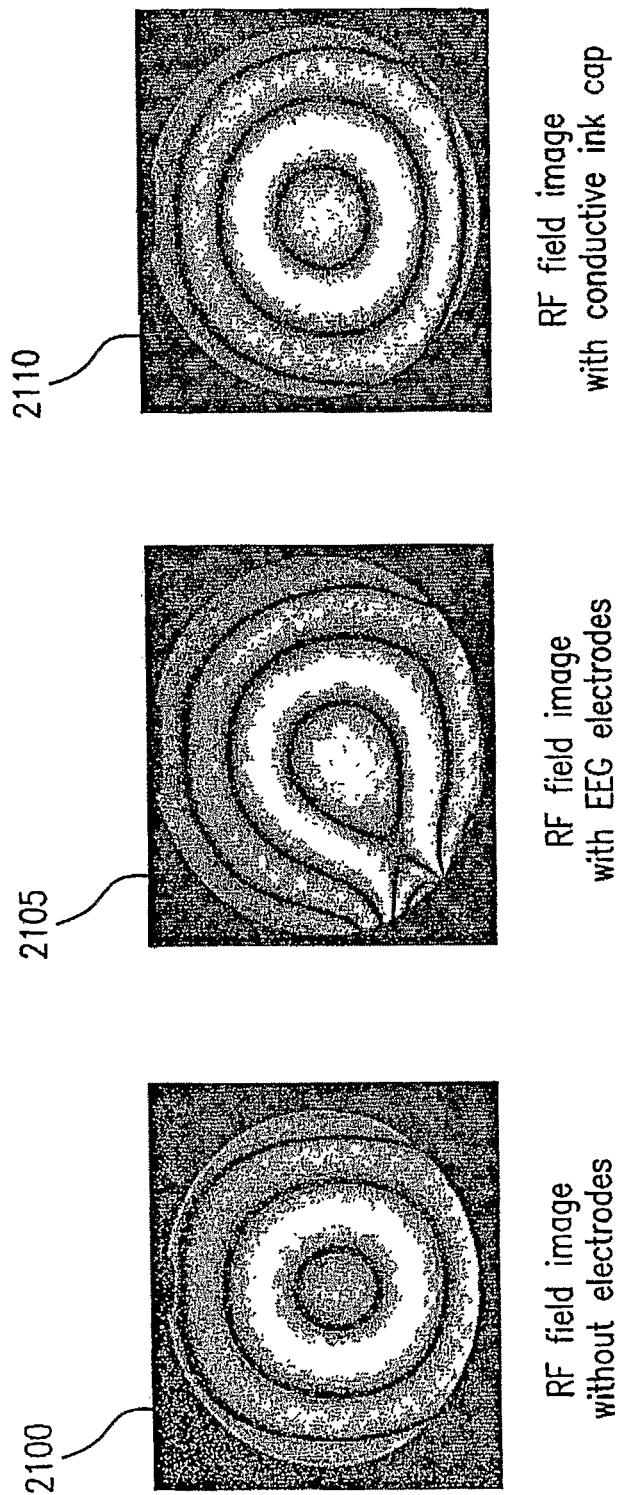
FIG. 21 is an exemplary RF field images of the spherical phantom that uses no electrodes, standard electrodes, and the conductive ink cap according to the exemplary embodiments of the present invention.

FIG. 21 shows exemplary RF field images 2100-2110 of the spherical phantom using no electrodes, standard electrodes, and the conductive ink cap according to the exemplary embodiments of the present invention. The RF field image 2100 is an RF field image acquired without electrodes, the RF field image 2105 is an RF field image acquired with a standard set of electrodes, and the RF field image 2110 is an RF field image acquired with the conductive ink cap of an exemplary embodiment of the present invention.

The RF field images 2100-2110 were obtained with an 18 cm diameter homogenous spherical phantom and the following sequences: (1) 2D spin echo with a single echo resulting in RF field maps, using TE=17 ms; FA=720°; TR=300 ms; FOV=300×300 mm$^2$; matrix=256×256; (2) structural MPRAGE using TE=3.42 ms; FA=7°; TR=2350 ms; FOV=276×276 mm$^2$; matrix=256×256; and (3) single shot gradient-echo EPI using TE=30 ms; FA=90°; TR=3510 ms; FOV=211×211 mm$^2$; matrix=64×64. Most of the preliminary MRI image quality studies were done at 3 T, given the higher distortions and image warping present at 7 T.

The images 2100-2110 show that the RF field maps ($B_1$ field) distortions were negligible for the case of the conductive ink cap. Additionally, the SNR comparison of the EPI images showed higher SNR when using the conductive ink cap as a replacement for the standard gold EEG electrode set.

The results illustrated in FIGS. 19-21 show that the conductive ink cap may improve subject's safety in high magnetic field recordings. The sensors and leads may cause lower temperature increase, compared to metallic or carbon fiber electrodes, and leads with the same input power. The conductive ink cap with the sensor system of the present invention can be safely used in high magnetic fields (7 T) due to of the minimal or no use of metals and the very weak interaction with RF fields generated by the MRI scanner.

Figure 22:
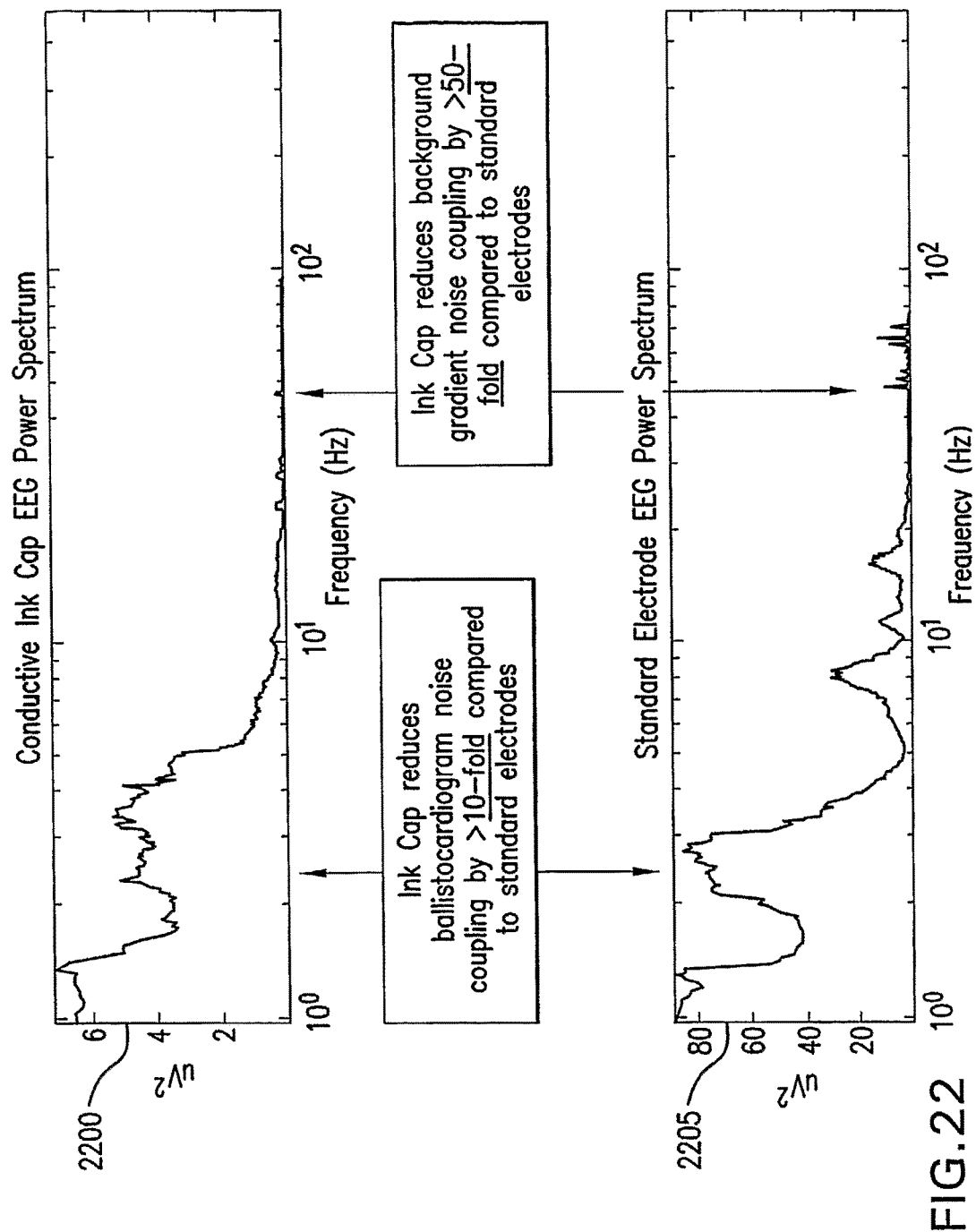
FIG. 22 are plots of an exemplary power spectrum of the EEG signals acquired using a standard electrode set and the conductive ink cap of the exemplary embodiment of the present invention.

FIG. 22 shows exemplary plots of 2200 and 2205 of power spectrum of the EEG signals acquired using a standard electrode set and the conductive ink cap of the present invention. The plot 2200 shows that using the conductive ink cap to perform EEG recordings concurrently with MRI scans can reduce the ballistocardiogram noise coupling by more than ten-fold as compared to the use of standard electrodes. The implementation of the conductive ink cap can also reduce the background gradient noise coupling by more than fifty-fold as compared to standard electrodes.

The foregoing descriptions of specific embodiments and best mode of the present invention have been presented for purposes of illustration and description only. They are not intended to be exhaustive or to limit the invention to the precise forms disclosed. Specific features of the invention are shown in some drawings and not in others, for purposes of convenience only, and any feature may be combined with other features in accordance with the invention. Steps of the described processes may be reordered or combined, and other steps may be included. The embodiments were chosen and described in order to best explain the principles of the invention and its practical application, to thereby enable others skilled in the art to best utilize the invention and various embodiments with various modifications as are suited to the particular use contemplated. Further variations of the invention will be apparent to one skilled in the art in light of this disclosure and such variations are intended to fall within the scope of the appended claims and their equivalents. The descriptions, disclosures and contents of all publications referred to herein are incorporated herein in their entireties.

What is claimed is:

1. A system for transmitting electrical signals to or from the head of a subject, the system comprising:
    an electrode carrier;
    a plurality of electrodes configured to transmit electrical signals and connected to the carrier, the carrier configured and arranged for placement on the head of the subject and, upon placement thereon, arranged to position the electrodes for transmitting electrical signals to or from the head;
    a conductive trace configured to be electrically connected to the subject to receive or deliver the electrical signals; and
    wherein each electrode includes a conductive lead electrically extending from the conductive trace to communicate the electrical signals, the conductive lead configured to be electrically isolated from the subject and extending to a connector, and the conductive lead constructed of a predetermined amount of a conductive ink forming a conductive ink layer, the predetermined amount of the conductive ink being substantially dispersed through the extent of the conductive lead, the predetermined amount of the conductive ink having a resistivity in a range of 1 kilo-ohm·meter to 100 kilo-ohm·meters, the resistivity of the predetermined amount of the conductive ink selected to reduce exposure from RF pulses used during magnetic resonance imaging.

2. The system of claim 1 further comprising a motion sensor configured to at least detect ballistocardiogram motion.

3. The system of claim 2 wherein the motion sensor includes a piezo-electric sensor.

4. The system of claim 2 wherein the motion sensor is connected to the electrode carrier.

5. The system of claim 1 wherein the conductive trace has a resistivity of at least 25 kilo-ohm·meters.

6. The system of claim 5 wherein the conductive trace and the conductive lead include at least one of carbon, silver, and silver chloride.

7. The system of claim 1 wherein the conductive trace and the conductive lead include a polymer thick film.

8. The system of claim 1 wherein the conductive trace forms a partial circle and the conductive lead is electrically connected to the conductive trace between two endpoints of the partial circle so as to reduce eddy currents induced by an applied RF signal.

9. The system of claim 1 wherein the conductive lead includes a plurality of layers including at least one of a foam layer, a polyester layer, a conductive ink layer, a dielectric layer, and a silicone layer.

10. The system of claim 1 wherein the carrier forms a stretchable cap.

11. The system of claim 10 wherein the stretchable cap includes a polyester substrate and having connected thereto a plurality of microstrips of conductive ink forming the conductive leads.

12. The system of claim 11 wherein the conductive ink is coated with dielectric ink.

13. The system of claim 12 wherein the carrier includes a vibration dampener including at least one of an elastic mesh dressing and a pillow.

14. The system of claim 11 wherein the conductive trace is connected to the polyester substrate.

15. The system of claim 1 wherein the conductive trace and the conductive lead are free of ferromagnetic materials.

16. The system of claim 1 configured and arranged for receiving electroencephalogram (EEG) signals.

17. The system of claim 1 configured and arranged for delivering stimulation to the subject.

18. The system of claim 1 wherein the conductive lead has a length between about 35 cm and 56 cm.

19. A system for delivering or receiving electrical signals to or from the head of a subject, the system comprising:

an electrode carrier;

a plurality of electrodes configured to communicate electrical signals and connected to the carrier, the carrier configured and arranged for placement on the head of the subject and, upon placement thereon, arranged to position the electrodes for transmitting electrical signals to or from the head;

a conductive trace configured to be electrically connected to the subject to communicate the electrical signals;

wherein each electrode includes a conductive lead electrically extending from the conductive trace to communicate the electrical signals, the conductive lead configured to be electrically isolated from the subject and extending to a connector;

wherein the conductive lead comprises a polymer thick film, the polymer thick film having a resistivity in a range of 1 kilo-ohm·meter to 100 kilo-ohm·meters, the resistivity of the polymer thick film selected to reduce exposure from RF pulses used during magnetic resonance imaging, said resistivity substantially dispersed through the extent of the conductive lead; and wherein the conductive trace forms a partial circle and the conductive lead is electrically connected to the conductive trace between two endpoints of the partial circle.

20. The system of claim 19 further comprising a motion sensor configured to at least detect ballistocardiogram motion.

21. The system of claim 20 wherein the motion sensor includes a piezo-electric sensor.

22. The system of claim 19 wherein the conductive trace has a resistivity of at least 25 kilo-ohm·meters.

23. The system of claim 19 wherein the conductive lead has a length between about 35 cm and 56 cm.

* * * * *